(12) United States Patent
Shimizu et al.

(10) Patent No.: US 6,312,418 B1
(45) Date of Patent: *Nov. 6, 2001

(54) ABSORBENT ARTICLE WRAPPER COMPRISING A SIDE FLAP FASTENER COVER

(75) Inventors: Yoshihisa Shimizu; Maki Hasegawa, both of Suita (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/381,707

(22) PCT Filed: Feb. 27, 1998

(86) PCT No.: PCT/IB98/00247

§ 371 Date: Nov. 5, 1999

§ 102(e) Date: Nov. 5, 1999

(87) PCT Pub. No.: WO98/42285

PCT Pub. Date: Oct. 1, 1998

(51) Int. Cl.[7] ....................................... A61F 13/15
(52) U.S. Cl. ................ 604/385.02; 604/385.04; 604/385.05
(58) Field of Search ............ 604/385.02, 385.04, 604/385.03, 385.01, 390, 387

(56) References Cited

U.S. PATENT DOCUMENTS

| 5,484,636 | * | 1/1996 | Berg, Jr. et al. | ........................ 428/40 |
| 6,074,376 | * | 6/2000 | Mills | ................................. 604/390 |
| 6,168,582 | * | 1/2001 | Hasegawa | ........................ 604/385.2 |

* cited by examiner

*Primary Examiner*—Aaron J. Lewis
*Assistant Examiner*—Jacqueline F Stephens
(74) *Attorney, Agent, or Firm*—Matthew P. Fitzpatrick; Kevin C. Johnson; Steven W. Miller

(57) ABSTRACT

An individually packaged absorbent article having a pair of first flaps and a pair of second flaps with fasteners, such as adhesive fasteners thereon, is disclosed. The absorbent article is wrapped by a wrapper for individually packaging the absorbent article. The wrapper comprises a main wrapper sheet and a flap fastener cover. Adhesive fasteners of the first and second flaps are releasably covered by the flap fastener cover which is joined to a part of the main wrapper sheet. The flap fastener cover protects the fasteners located on the first and second flaps of the absorbent article. The main wrapper sheet overlays one major surface of the absorbent article and by folding the article and sealing the wrapper in that folded orientation, an individually packaged disposable absorbent article is provided.

20 Claims, 21 Drawing Sheets

ABSORBENT ARTICLE WRAPPER COMPRISING A SIDE FLAP FASTENER COVER

FIELD OF INVENTION

This invention relates to an absorbent article individually packaged by a wrapper comprising a main wrapper sheet for the absorbent article and a flap fastener cover for flap fasteners of flaps. More particularly, this invention relates to an absorbent article comprising a pair of first flaps and a pair of second flaps apart from the first flaps in the longitudinal direction of the absorbent article, wherein each flap comprises flap fasteners, and the flap fasteners are covered by the flap fastener cover.

BACKGROUND

An absorbent article such as a sanitary napkin comprising a pair of flaps which extend laterally outward from an absorbent means is well known. One type of such an absorbent article comprises a pair of flaps which extend laterally outward from a central region of both longitudinal side edges of an absorbent means. The flaps are intended to be folded around the edges of a wearer's undergarment in the crotch region. Thus, in use the flaps are disposed between the edges of the wearer's undergarment in the crotch region and the wearer's thighs. Commonly, the flaps are provided with flap fasteners such as adhesive for affixing the flaps to the underside of the wearer's undergarment. The flaps serve at least two purposes. First, the flaps prevent exudates which otherwise would soil the edges of the wearer's undergarment from doing such, Second, the flaps help stabilize the napkin from shifting out of the position chosen by the wearer. This is especially so when the flaps are affixed to the underside of the undergarment.

The flaps of such sanitary napkins may be folded onto the topsheet side or the backsheet side to conserve space during packaging, i.e., the period between manufacture of the sanitary napkin and its intended first use by the wearer. At the time of the first use by the wearer, the flaps are usually unfolded to facilitate installation of the sanitary napkin into the wearer's undergarment. The flap fasteners of the folded flaps are usually covered by a flap fastener cover so as not to inadvertently adhere to each other or another part of the product before the sanitary napkin is used. When the flaps are folded onto the topsheet side, the flap fasteners of the flaps face outside and are covered by the flap fastener cover thereby bridging the flaps to each other over the topsheet. Japanese Laid-open Patent publication H5-293139 published on Nov. 9, 1993, Japanese Laid-open Patent publication H6-78953 published on Mar. 22, 1994 and Japanese Laid-open Utility-Model publication H6-26835 published on Apr. 12, 1994 disclose sanitary napkins having flaps which are folded onto the topsheet and flap fasteners which are covered by a flap fastener cover. The sanitary napkins disclosed therein further comprise a main fastener for securing the sanitary napkin to the inside of the wearer's undergarment. The main fastener is also covered by a main fastener cover. Therefore, when the sanitary napkin is used, the wearer must remove both the flap fastener cover and the main fastener cover. The wearer must then properly dispose of the various fastener covers to prevent them from becoming litter.

Attempts to facilitate removal of a flap fastener cover and a main fastener cover from the sanitary napkin have been made. Japanese Laid-open Utility-Model publication H5-9526 published on Feb. 9, 1993 and Japanese Laid-open Utility-Model publication H5-9529 published on Feb. 9, 1993 disclose sanitary napkins comprising a sanitary napkin main body with a main body fastener, flaps with flap fasteners and a fastener cover for covering the flap fasteners and the main fastener. The fastener cover comprises flap fastener cover portions and a main fastener cover portion which are connected to each other. Therefore, as the main fastener cover portions are removed from the sanitary napkin main body, the flap fastener cover portion is also removed from the flaps. This publication, however, does not disclose arrangements for absorbent articles having a wrapper for individually packaging the absorbent article.

Other attempts to facilitate removal of a flap fastener cover and/or a main fastener cover from a sanitary napkin main body have been made in connection with removal of a wrapper for individually packaging the sanitary napkin. Japanese Laid-open Utility-Model publication H6-26833 published on Apr. 12, 1994 discloses a sanitary napkin comprising a sanitary napkin main body with a main fastener, flaps with flap fasteners, a wrapper for packaging the sanitary napkin main body, a flap fastener cover and a main fastener cover. The main fastener cover is connected to a part of the wrapper so that the main fastener cover is removed from the main body as the sanitary napkin main body is taken out from the wrapper. However, the flap fastener cover also must be removed from the flaps.

Japanese Laid-open Utility-Model H7-39820 published on Jul. 18, 1995 discloses a sanitary napkin comprising a sanitary napkin main body having a topsheet, a backsheet, and an absorbent core. The sanitary napkin also comprises a pair of flaps which are folded around the edges of a wearer's undergarment in the crotch region when the sanitary napkin is used. Adhesive layers provided with the main body and the flaps are covered by an adhesive layer cover which may comprise a wrapper for individually packaging the sanitary napkin. The flaps are folded to the inside of the main body. The adhesive layer cover covering the adhesive layers of the main body extends beyond the longitudinal sides and transverse edges of the main body. The adhesive layer cover extends beyond one transverse end and the extending portion of the adhesive layer cover is folded toward the inside to cover the adhesive layers of the flaps. Japanese Laid-open Utility-Model H6-75446 published on Jul. 18, 1995 discloses a sanitary napkin comprising a sanitary napkin main body and a pair of flaps extending laterally outward from the both sides in the longitudinal direction of the sanitary napkin. The flaps are folded onto a body facing side of the sanitary napkin before the sanitary napkin is used, and are folded around the edges of a wearer's undergarment in the crotch region when the sanitary napkin is used. A garment facing side of the sanitary napkin provided with an adhesive layer is wrapped by a wrapper releasably treated. The wrapped sanitary napkin is folded together with the wrapper about a folding line. This publication further discloses a packaging structure for the sanitary napkin where a part of the wrapper covers the adhesive layers of the flaps. Namely, the transverse edge of the wrapper extends beyond the end edge of the sanitary napkin and is folded towards the adhesive layers of the flaps which are folded onto the topsheet. European Patent publication EP 0 750 896 A2 published on Jan. 2, 1997 discloses a sanitary napkin comprising a napkin body and a pair of flaps extending from transversely opposite side edges of the napkin body. The napkin body is folded longitudinally thereof in a three layer overlapping relationship and the flaps are also folded onto a top surface of the napkin body. Release sheets are releasably bonded onto adhesive zones provided on back surfaces of the napkin body and the flaps, respectively. A wrapping sheet is also folded together with the napkin body so as to wrap the napkin body as well as the flaps, wherein the respective release sheets are fixedly bonded to an inner surface of the wrapping sheet so that the wrapping sheet and the release sheet can be peeled off in the form of an integrated strip-like sheet from the napkin when picking out the napkin from the wrapping sheet. These publications, however, do not disclose arrangements for absorbent articles having another pair of flaps apart from the flaps in the longitudinal direction of the absorbent article.

Another type of an absorbent article comprises a pair of flaps which extend laterally outward from a back region of both longitudinal side edges of an absorbent means. The flaps of the second type of an absorbent article are intended to stay widespread in a back region of the inside of a wearer's undergarment. In use, the flaps are disposed between the wearer's hips and the wearer's undergarment. The flaps of the second type of an absorbent article also prevent exudates which otherwise would soil the back region of the wearer's undergarment. The flaps may be provided with flap fasteners such as adhesive for affixing the flaps to the inside of the wearer's undergarment to stabilize the napkin shifting in the back region of the wearer's undergarment. The flap fasteners may be covered by a flap fastener cover not to inadvertently adhere to each other or another part of the product before the sanitary napkin is used. Japanese Laid-open Patent publication H8-224269 published on Sep. 3, 1996 discloses an individually packaged sanitary napkin. The sanitary napkin comprises a topsheet, a backsheet, an absorbent core, a pair of back flap portions having adhesive layers on both back sides in the longitudinal direction of the sanitary napkin, and a main adhesive layer covered by a main release paper. The back flap portions are folded onto the topsheet side so that the adhesive layers of the back flap portions face upwardly and a flap release paper is attached on the adhesive layers. A wrapper is joined to the non-releasably treated surface of the main release paper by using a first adhesive. The sanitary napkin is folded into three regions together with the wrapper so that the flap release paper faces the backsheet side of the front portion of the sanitary napkin. The wrapper covering the front portion of the sanitary napkin is joined to the non-releasably treated surface of the flap release paper by using a second adhesive. This publication, however, does not disclose arrangements for absorbent articles having another pair of flaps apart from the flaps in the longitudinal direction of the absorbent article.

While prior art absorbent articles such as sanitary napkins have addressed some of the problems of achieving an individually packaged absorbent article, they have not addressed the problems to the extent of or in the manner of the present invention. Therefore, a primary object of the present invention is to provide an improved individually packaged absorbent article.

SUMMARY

The present invention provides an individually packaged absorbent article comprising: (a) an absorbent article extending in a longitudinal direction and comprising a main body portion having a pair of longitudinal side edges, a pair of end edges, a garment surface, and a body surface, wherein the garment surface of the main body portion may be placed in a wearer's undergarment, and the absorbent article comprises a pair of first flaps joined to the main body portion and extending laterally outward beyond the longitudinal side edges of the main body portion and a pair of second flaps joined to the main body portion apart from the first flaps in the longitudinal direction and extending laterally outward beyond the longitudinal side edges of the main body portion, wherein the garment surface of each of the first and second flaps comprises a first flap fastener and a second flap fastener respectively, and the first and second flaps are folded over the body surface of the main body portion to expose the flap fasteners; (b) a wrapper for the absorbent article, the wrapper comprising a main wrapper sheet and a flap fastener cover, wherein (c) the main wrapper sheet comprises a pair of longitudinal side portions, a pair of end portions, an inner surface facing the main body portion and an outer surface, the main wrapper sheet is positioned adjacent to the garment surface of the main body portion, the main wrapper sheet and the main body portion of the absorbent article comprise two transverse axes and three regions divided by the two axes, wherein the three regions comprise a first region into which a majority of the first flaps extends, a second region into which a majority of the second flaps extends and a third region, and the two transverse axes comprise the first axis extending laterally between the first region and the second region and the second axis extending laterally between the first region and the third region, (d) the flap fastener cover comprises a pair of longitudinal side portions, a pair of end portions, a releasable surface facing the flap fasteners of the first and second flaps, an opposing surface, a first portion, and a second portion, wherein a majority of the first portion extends in the first region and a majority of the second portion extends in the second region when the absorbent article is folded at the transverse axes, and the flap fastener cover is releasably affixed to the flap fasteners of the first and second flaps, (e) the end portion of the first portion of the flap fastener cover is joined to the end portion of the main wrapper sheet of the second region.

The present invention further provides an individually packaged absorbent article comprising: (a) an absorbent article extending in a longitudinal direction and comprising a main body portion having a pair of longitudinal side edges, a pair of end edges, a garment surface, and a body surface, wherein the garment surface of the main body portion may be placed in a wearer's undergarment, and the absorbent article comprises a pair of first flaps joined to the main body portion and extending laterally outward beyond the longitudinal side edges of the main body portion and a pair of second flaps joined to the main body portion apart from the first flaps in the longitudinal direction and extending laterally outward beyond the longitudinal side edges of the main body portion, wherein the garment surface of each of the first and second flaps comprises a first flap fastener and a second flap fastener respectively, and the first and second flaps are folded over the body surface of the main body portion to expose the flap fasteners; (b) a wrapper for the absorbent article, the wrapper comprising a main wrapper sheet and a flap fastener cover, wherein (c) the main wrapper sheet comprises a pair of longitudinal side portions, a pair of end portions, an inner surface facing the main body portion and an outer surface, the main wrapper sheet is positioned adjacent to the garment surface of the main body portion, the main wrapper sheet and the main body portion of the absorbent article comprise two transverse axes and three regions divided by the two axes, wherein the three regions comprise a first region into which a majority of the first flaps extends, a second region into which a majority of the second flaps extends and a third region, and the two transverse axes comprise the first axis extending laterally between the first region and the second region and the second axis extending laterally between the first region and the third region, (d) the flap fastener cover comprises a pair of longitudinal side portions, a pair of end portions, a top surface facing the flap fasteners of the first and second flaps, an opposing surface, a first portion, and a second portion, wherein a majority of the first portion extends in the first region and a majority of the second portion extends in the second region when the absorbent article is folded at the transverse axes, and the flap fastener cover is releasably affixed to the flap fasteners of the first and second flaps, (e) the first portion and the second portion of the flap fastener cover are joined to one another so that the majority of the first portion of the flap fastener cover is disposed on the majority of the second portion of the flap fastener cover with face-to-face relation, and (f) one of the end portions of the flap fastener cover is joined to the end portion of the main wrapper sheet of the second region.

DETAILED DESCRIPTION OF THE INVENTION

Figure 1:
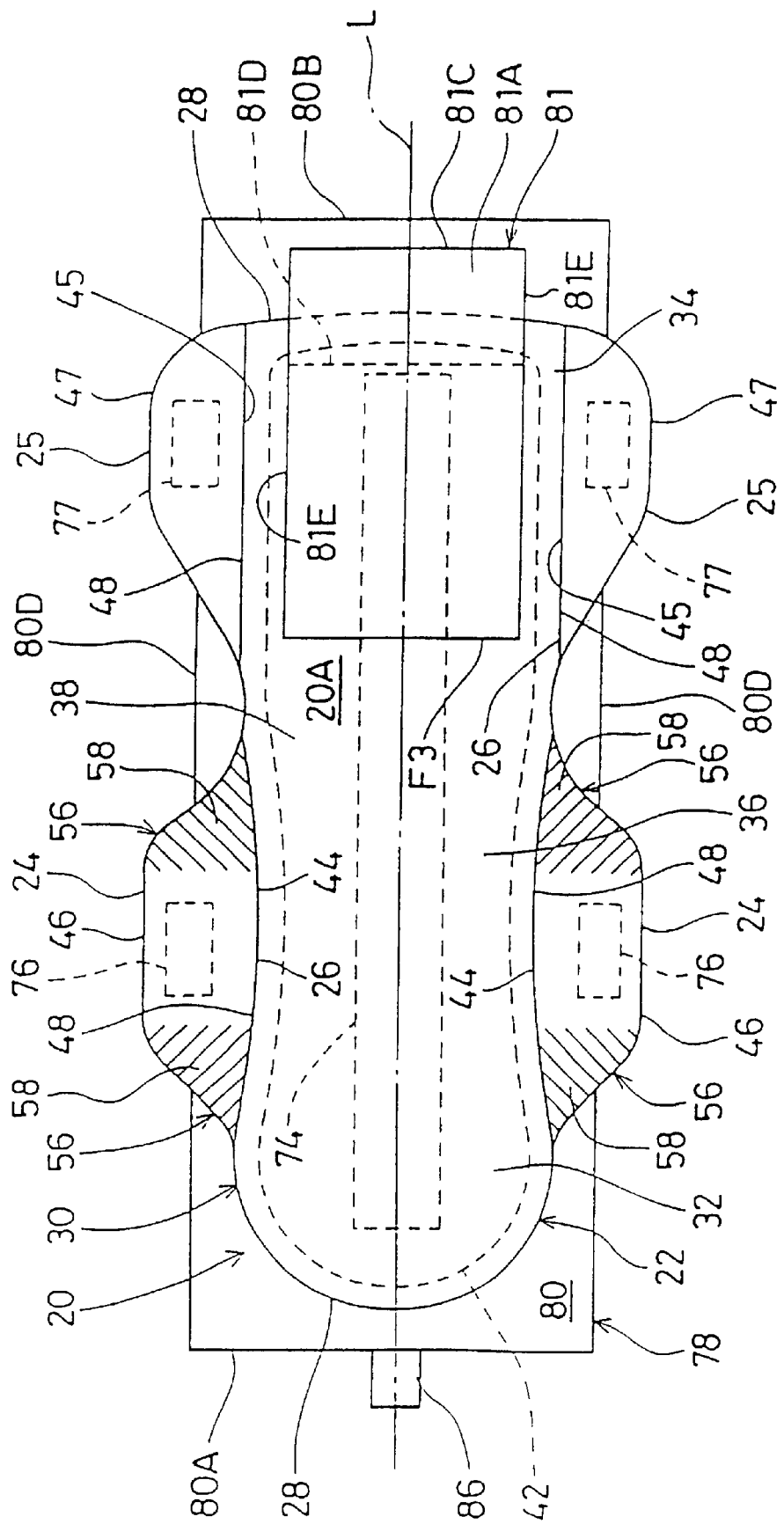
FIG. 1 is a top plan view of one embodiment of the wrapper of the present invention in an opened position with a preferred sanitary napkin disposed thereon and the flaps of the sanitary napkin outstretched.
Figure 2:
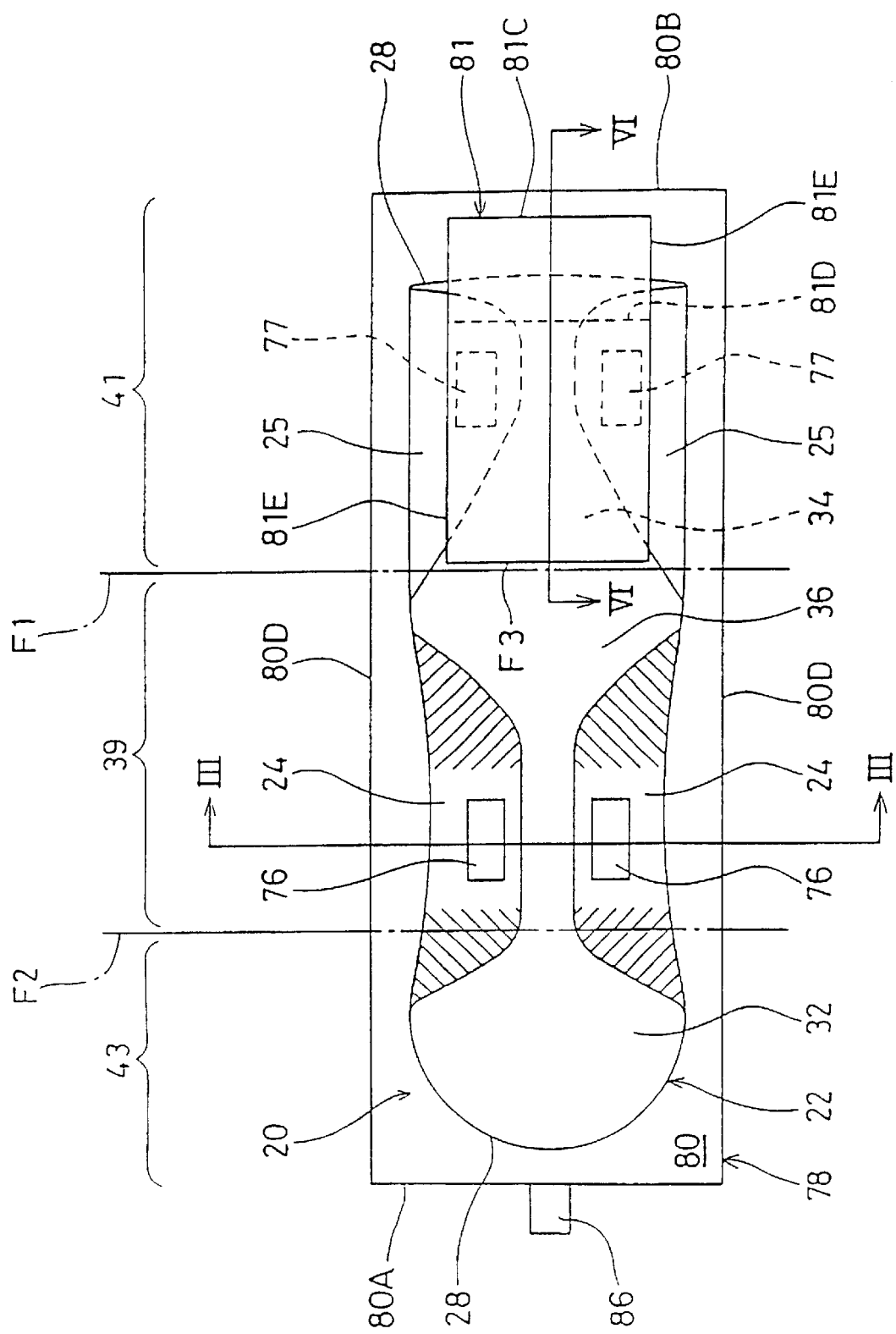
FIG. 2 is a top plan view of the wrapper of the present invention shown in FIG. 1 with the flaps of the sanitary napkin folded over the topsheet.
Figure 3:
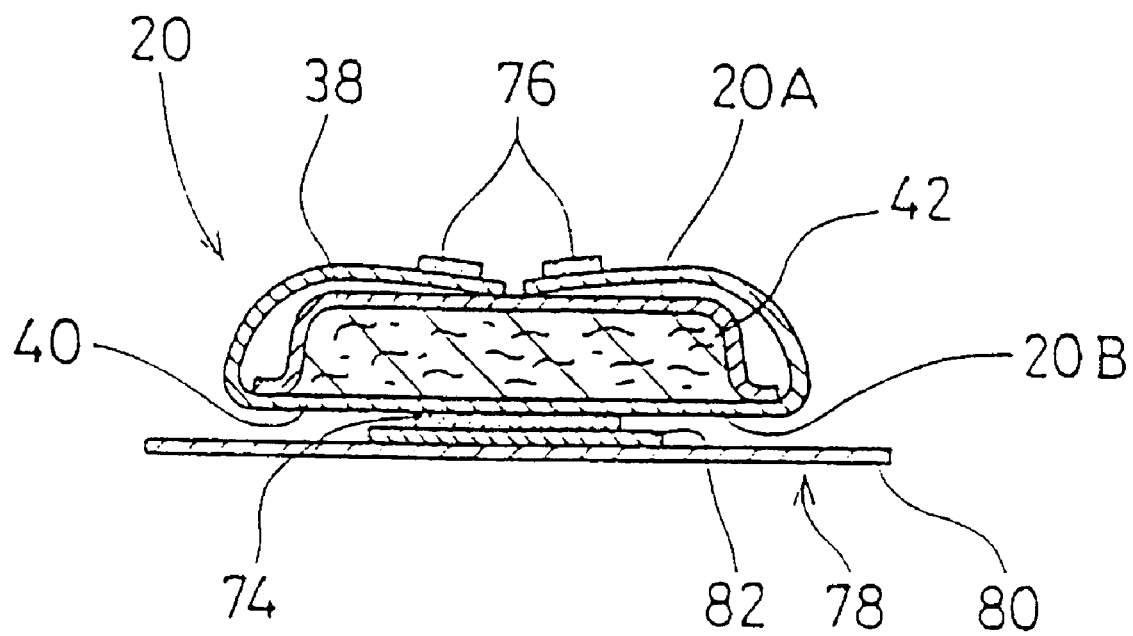
FIG. 3 is a cross-sectional view of FIG. 2 taken along the line III—III.

Referring now to the drawings, the present invention is embodied in a preferred but non-limiting embodiment. As shown in FIGS. 1, 2, and 3, the invention comprises a wrapper 78 for a disposable absorbent article, particularly a sanitary napkin 20.

The sanitary napkin 20 is used to collect vaginal discharges, such as menses, and prevent soiling of the wearer's clothing by such discharges. As shown in FIGS. 1 and 2, the sanitary napkin 20 basically comprises a main body portion 22 and first flaps 24 and second flaps 25. The main body portion 22 of the sanitary napkin 20 may have a fastener, such as a pressure sensitive adhesive fastener 74 thereon for fastening the main body portion 22 in the wearer's undergarment. The first flaps 24 preferably each have first fasteners thereon, such as a pressure sensitive adhesive fastener 76, for releasably affixing the first flaps 24 of the sanitary napkin 20 in a configuration folded around the edges of the crotch of the wearer's undergarment. The second flaps 25 preferably each have second fasteners thereon, such as a pressure sensitive adhesive fastener 77, for releasably affixing the second flaps 25 of the sanitary napkin 20 in a configuration staying widespread in a back region of the inside of a wearer's undergarment. The wrapper 78 of the present invention serves to cover and protect the first flap fasteners 76, the second flap fasteners 77, and the main body fastener 74 (if there is one), and is folded around the sanitary napkin 20 to provide an individual package for the sanitary napkin 20. Before looking at the characteristics of the wrapper 78 in greater detail, the properties of the sanitary napkin 20 will be briefly discussed.

The sanitary napkin 20 (and the main body portion 22 thereof) has two surfaces, a liquid previous body-contacting surface or "body surface" 20A that is intended to be worn adjacent to the body of the wearer, and a liquid impervious garment surface 20B. The sanitary napkin 20 is shown in FIG. 1 as viewed from its body surface 20A. The sanitary napkin 20 has two centerlines, a principal longitudinal centerline L and a principal transverse centerline (not shown in FIG. 1). The term "longitudinal," as used herein, refers to a line, axis or direction in the plane of the sanitary napkin 20 that is generally aligned with (e.g. approximately parallel to) a vertical plane which bisects a standing wearer into left and right body halves when the sanitary napkin 20 is worn. The terms "transverse," "lateral" or "width" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the first flaps 24 and the second flaps 25. The main body portion 22 has two spaced apart longitudinal edges 26, two spaced apart transverse or end edges (or "ends") 28, which together form the periphery 30 of the main body portion. The main body portion 22 also has three sections comprising a central section (first section) 36, one end section (second section) 34 and the other end section (third section) 32. The first section 36 is disposed between the second section 34 and the third section 32. The second section 34 and the third section 32 extend outwardly in the longitudinal direction from the edges of the central section 36 of the main body portion 22. When the sanitary napkin 20 is individually packaged, the main body portion 22 and the wrapper 78 are folded into three regions comprising a first region 39, a second region 41, and a third region 43 divided by two fold axes F1 and F2 (refer to FIG. 2). The first section 36, the second section 34 and the third section 32 of the main body portion 22 generally extend in the first region 39, the second region 41 and the third region 43, respectively.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the wrapper of the present invention is not limited to use with absorbent articles of the type or having the specific configurations shown in the drawings.

FIG. 3 shows the individual components of the main body portion 22 of the sanitary napkin 20. The main body portion 22 of the sanitary napkin 20 preferably comprises at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations).

Suitable materials for the components of the main body portion 22, and some of the various configurations in which such components can be assembled are described generally in U.S. Pat. No. 4,321,924, entitled "Bordered Disposable Absorbent Article" issued to Ahr on Mar. 30, 1982; U.S. Pat. No. 4,425,130, entitled "Compound Sanitary Napkin" issued to DesMarais on Jan. 10, 1984; U.S. Pat. No. 4,950, 264, entitled "Thin, Flexible Sanitary Napkin" issued to Osborn on Aug. 21, 1990: U.S. Pat. No. 5,308,346, entitled "Elasticized Sanitary Napkin" issued to Sneller, et al. on May 3, 1994; and U.S. Pat. No. 5,389,094, entitled "Absorbent Article Having Flaps and Zones of Differential Extensibility" issued to Lavash, et al. on Feb. 14, 1995. The main body portion 22 of the sanitary napkin 20 may also be comprised of one or more extensible components such as those sanitary napkins, and the like described in U.S. patent application Ser. Nos. 07/915,133 and 07/915,284, both filed Jul. 23, 1992, in the name of Osborn, et al. (PCT Publication Nos. WO 93/01785 and 93/01786, both published Feb. 4, 1993).

FIGS. 1–3 show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 30. The topsheet 38 is preferably joined to the body-facing side of the absorbent core 42 and the backsheet 40 is preferably joined to the garment-facing side of the absorbent core 42. The topsheet 38 and backsheet 40 can be joined to the absorbent core 42 in any suitable manner known in the art for this purpose, such as by an open pattern of adhesives. The portions of the topsheet 38 and backsheet 40 that extend beyond the edges of the absorbent core 42 are preferably also joined to each other. These portions of the topsheet 38 and backsheet 40 can also be joined in any suitable manner known in the art. Preferably, in the embodiment shown, these portions of the topsheet 38 and backsheet 40 are joined using adhesives over substantially the entire portions that extend beyond the edges of the absorbent core 42, and a crimp seal around the periphery 30 of the main body portion 22 where the topsheet 38 and backsheet 40 are densified by the application of pressure or heat and pressure.

The sanitary napkin 20 shown in FIGS. 1–3, as discussed above, also comprises a pair of first flaps 24 and a pair of second flaps 25 that are joined to the main body portion 22. The first flaps 24 extend laterally outward beyond the longitudinal side edges 26 of the main body portion 22 from their proximal edges 44 to their distal edges (or "free ends") 46. The first flaps 24 extend laterally outward from at least a part of the first section 36 of the main body portion 22 and majority of the first flaps 24 extends in the first region 39 divided by the fold axes F1 and F2. The second flaps 25 extend laterally outward beyond the longitudinal side edges 26 of the main body portion 22 from their proximal edges 45 to their distal edges (or "free ends") 47. The second flaps 25 are positioned adjacent to one end edge 28 of the main body portion 22 apart from the first flaps 24 in the longitudinal direction of the main body portion 22. The second flaps 25 extend laterally from at least a part of the second section 34 of the main body portion 22 and majority of the second flaps 25 extend in the second region 41 divided by the fold axis F2.

The first flaps 24 and the second flaps 25 can be joined to the main body portion 22 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIGS. 1–3, the first flaps 24 and the second flaps 25 are integral with the main body portion 22 (that is, the flaps 24 and 25 comprise integral extensions of the backsheet 40. Alternatively, the flaps 24 and 25 may comprise integral extensions of the topsheet 38 and the backsheet 40.).

In other alternative embodiments, the flaps 24 and 25 can comprise one or more separate components that are joined to the garment-facing side of the main body portion 22. Preferably, in such a case, the flaps 24 and 25 each comprise a separate component that is joined to the garment-facing side of the main body portion 22. In such alternative embodiments, the flaps 24 and 25 are preferably otherwise unattached to the garment-facing side of the main body portion 22 of the sanitary napkin 20 between the points where they are attached to the main body portion 22 and the longitudinal side edges 26 of the main body portion 22. The flaps 24 and 25 in these latter embodiments can be joined to the garment-facing side of the main body portion 22 by any suitable attachment mechanism. Suitable attachment mechanisms include, but are not limited to adhesives, and the like. The first flaps 24 and the second flaps 25 may be joined to the main body portion 22 by different attachment method from each other.

The places or regions on the sanitary napkin 20 where the flaps 24 and 25 are joined to (or extend from) the main body portion 22, are referred to herein as "junctures". These regions will typically be longitudinally-oriented (or "longitudinal") junctures, such as lines of juncture 48. These regions can be any of various curved or straight lines, but they are not limited to lines. Thus, the junctures can comprise flanges, strips, intermittent lines, and the like.

The first flaps 24 and the second flaps 25 may be of any configuration desired, with one preferred configuration being shown in FIG. 1. FIG. 1 shows that the first flaps 24 are provided with zones of extensibility (or "zones of differential extensibility") 56 in the front edge and the back edge of each flap 24. The zones of extensibility 56 relieve stresses which are created in the first flaps 24 by the folding of the first flaps 24 around the crotch of the wearer's undergarment. The zones of extensibility 56 thereby help eliminate bunching of the first flaps 24 caused by said stresses. Preferably, in the embodiment shown in FIG. 1, the zones of extensibility 56 comprise pre-corrugated or "ring rolled" regions of the first flaps 24 in which the corrugations 58 define ridges and valleys that are oriented at an angle to the principal longitudinal centerline L. Suitable structures for providing the flaps 24 with zones of extensibility 56 are described in greater detail in U.S. Pat. No. 5,389,094 issued to Lavash, et al. and in commonly assigned copending U.S. patent application Ser. No. 08/380,769, entitled "Absorbent Article Having Flaps With Gathered Portions" filed in the name of Sue A. Mills, et al. on Jan. 30, 1995.

The sanitary napkin 20 preferably also has fasteners for securing the sanitary napkin 20 in place in a wearer's undergarment. FIGS. 1 and 2 show a preferred arrangement of fasteners which comprises a main body portion (or central pad) fastener, such as central pad adhesive 74, and flap fasteners, such as first flap adhesives 76 and second flap adhesives 77. The fasteners used with the sanitary napkin 20 are not limited to adhesive fasteners. Any suitable type of fastener known in the art can be used for this purpose. For example, the sanitary napkin 20 could be secured in place in a wearer's undergarment by mechanical fasteners, such as VELCRO®, or by a combination of adhesive and mechanical fasteners. For simplicity, however, the fasteners will be described in terms of adhesive fasteners and these fasteners are preferably pressure sensitive adhesive fasteners. Suitable pressure sensitive adhesive fasteners are described in greater detail in U.S. Pat. No. 4,917,697.

The central pad adhesive 74, the first flap adhesives 76 and the second flap adhesives 77 can be provided in any suitable configuration. In the preferred embodiment shown, the central pad adhesive 74 is provided in the form of a longitudinally oriented strip of adhesive that is centered about the principal longitudinal centerline L. The first flap adhesives 76 and the second flap adhesives 77 are provided in the form of a generally rectangular patch of adhesive on each first flap 24 and each second flap 25 respectively. The central pad adhesive 74 provides an adhesive attachment means for securing the main body portion 22 of the sanitary napkin 20 in the crotch portion of a panty. The first flap adhesives 76 are used to assist in maintaining the first flaps 24 in position after they are wrapped around the edges of the crotch portion of the panty. The second flap adhesives 77 are used to assist in maintaining the second flaps 25 in position after they are rendered widespread in a back region of the inside of the panty. The flaps can be maintained in position by attaching the flaps 24 to the undergarment, or to the opposing flap.

FIGS. 1–4 and 6–7 show one preferred version of the wrapper 78 of the present invention. As shown in FIG. 1, the wrapper, generally designated by reference number 78 comprises several elements. These elements can comprise integral portions of a single member or article, or they can comprise separate components joined to a member or article. The elements comprising the wrapper 78 include: a main wrapper sheet 80; an optional release component, such as a release paper (or release coating) 82 disposed on one side of the main wrapper sheet 80; a flap fastener cover, such as a flap adhesive cover 81.

Figure 7:
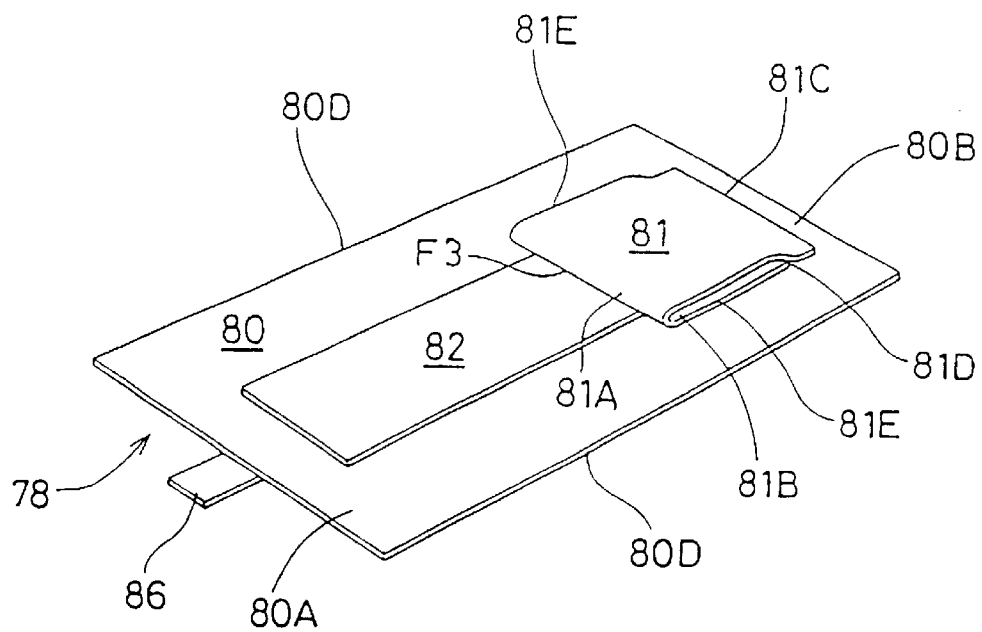
FIG. 7 is a perspective view of one preferred wrapper of the present invention.

The main wrapper sheet 80 (or "wrapper sheet") is the portion of the wrapper 78 which will be folded around the sanitary napkin 20 to provide an individual package for the sanitary napkin 20. The main wrapper sheet 80 preferably covers and is releasably attached to the central pad adhesive 74. The main wrapper sheet 80 preferably has dimensions that are slightly larger than those of the main body portion 22 of the sanitary napkin 20. Preferably, as shown in FIGS. 1, 2 and 7, the main wrapper sheet 80 has longitudinal side portions 80D which extend beyond the longitudinal side edges 26 of the main body portion 22 of the sanitary napkin 20. The main wrapper sheet 80 preferably also has a first end portion 80A and a second end portion 80B which extend beyond the end edges 28 of the main body portion 22 of the sanitary napkin 20. It is recognized, however, that satisfactory protection of sanitary napkin 20 may be afforded by a wrapper which is not larger than the main body portion 22 of the sanitary napkin 20.

The main wrapper sheet 80 can be made from any suitable material. The main wrapper sheet 80 is preferably manufactured from a thin flexible material which is liquid impermeable so that the wrapper 78 will be suitable for wrapping and disposing of a used sanitary napkin 20. For example, polyethylene films have been found to work well.

Figure 6:
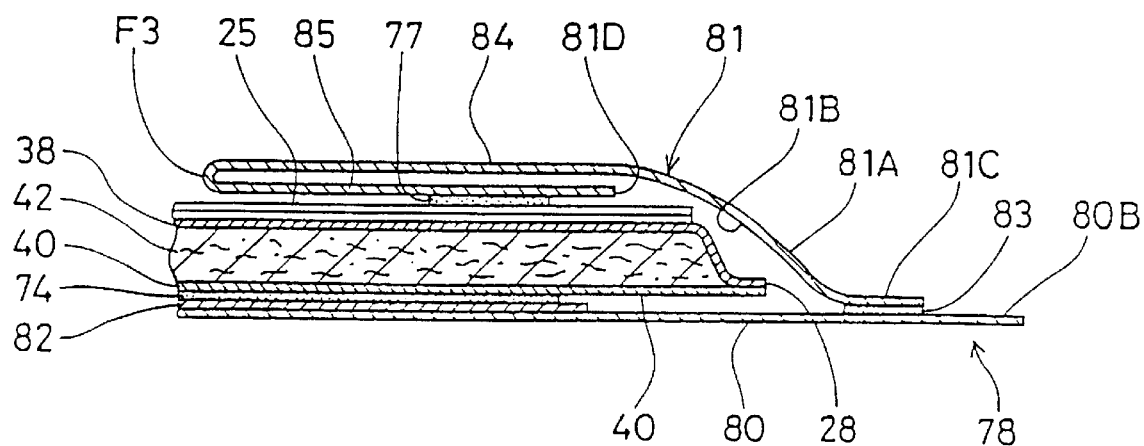
FIG. 6 is a cross-sectional view of FIG. 2 taken along the line VI—VI.

The main wrapper sheet 80 can be provided with the optional release component, such as release paper (or release coating) 82 so that the main wrapper sheet 80 will release from the central pad adhesive 74 when the wearer removes the sanitary napkin 20 from the wrapper 78. If a separate release paper is used, it can comprise any suitable material known in the art for this purpose, such as coated papers. Suitable release papers are described in U.S. Pat. No. 4,917,697. Such a release paper 82 can be laminated to the inside surface of the main wrapper sheet 80 as shown in FIGS. 3 and 6. If a release coating is used, the coating can be applied directly to the inside surface of the main wrapper sheet 80. Such a coating can comprise any material known in the art for this purpose, with silicone coatings being preferred. If a coating is used, the coating 82 may be provided by coating only that zone of the main wrapper sheet 80 which will substantially contact the central pad adhesive 76. Alternatively, the entire inside surface of the main wrapper sheet 80 may be coated. Coating the entire inside of a wrapper is disclosed in U.S. Pat. No. 5,181,610 entitled "Flexible Container with Nonstick Interior" which issued to Quick et al. on Jan. 26, 1993.

The flap adhesive cover (or "flap release strip") 81 covers and protects the first flap adhesives 76 and the second flap adhesives 77, and maintains the first flaps 24 and the second flaps 25 in position folded over the topsheet 38 for packaging. In the preferred embodiment shown in FIGS. 1, 2, 6 and 7, the flap adhesive cover 81 extends from the second end portion 80B of the main wrapper sheet 80 and generally extends in the second region 41 in a folded state. The flap adhesive cover 81 is preferably joined to the main wrapper sheet 80.

Figure 4:
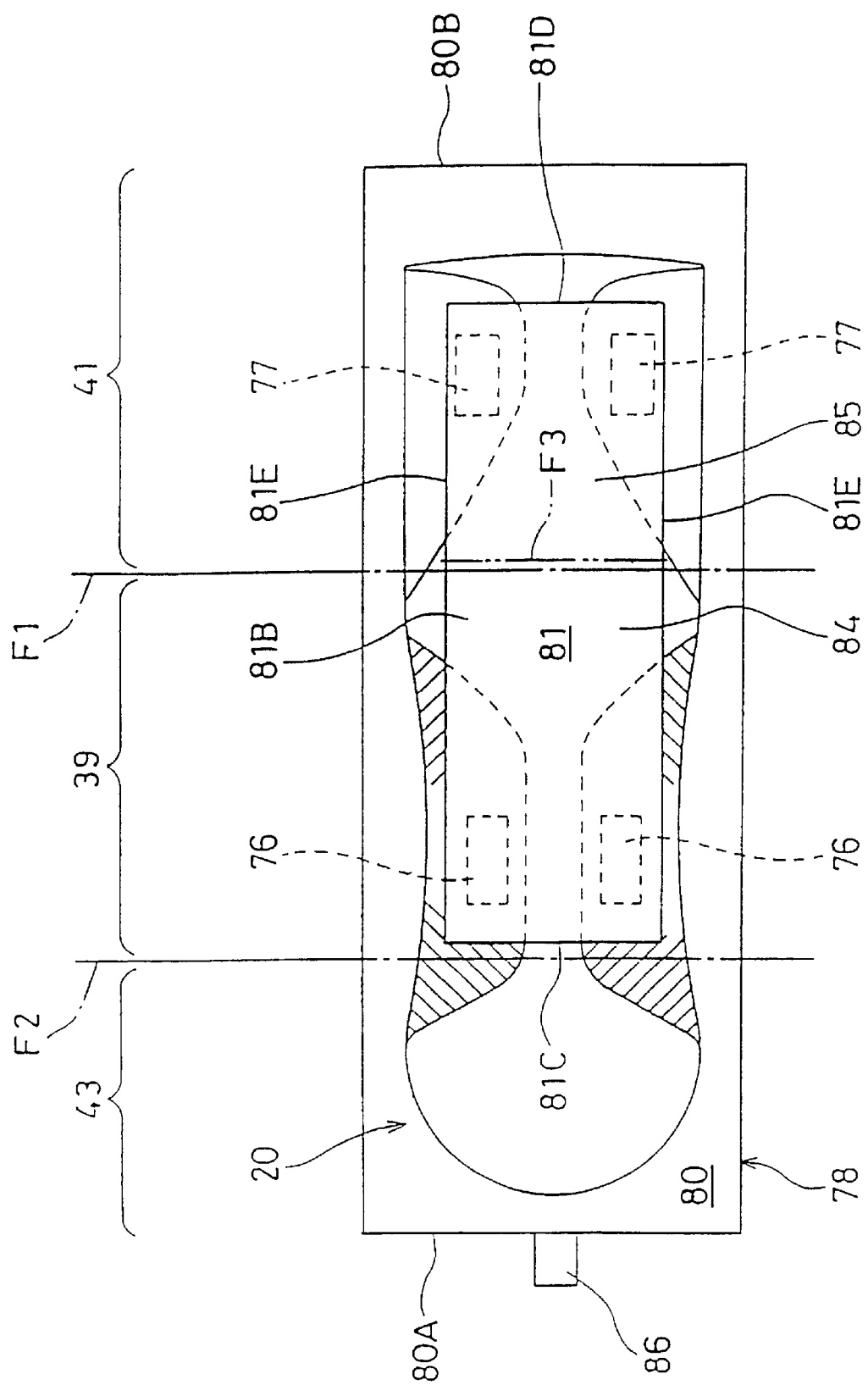
FIG. 4 is a top plan view of the wrapper of the present invention shown in FIG. 1 before the flap fastener cover and the main wrapper sheet are joined.

More concretely, as shown in FIG. 4, the flap adhesive cover 81 preferably extends in the first region 39 and the second region 41 in a stretched state before the flap adhesive cover 81 is folded and joined to the main wrapper sheet 80. The flap adhesive cover 81 preferably comprises a single separate sheet having a first end portion 81C, a second end portion 81D and a pair of longitudinal side portions 81E. The flap adhesive cover 81 also comprises a transverse fold axis F3, a first portion 84 and a second portion 85. The transverse fold axis F3 divides the flap adhesive cover 81 into the first portion 84 and the second portion 85. The first portion 84 extends from the transverse fold axis F3 toward the fold axis F2 in the first region 39 and the second portion 85 extends from the transverse fold axis F3 toward the second end portion 80B of the main wrapper 80 in the second region 41. The first portion 84 covers and protects the first flap adhesives 76 and the second portion 85 covers and protects the second flap adhesives 77.

The flap adhesive cover 81 also has two faces, one of which is a non-stick face (or releasable face) 81A, which is capable of releasable attachment with the flap fasteners, and an opposite face or side 81B. Preferably, as shown in FIG. 4, the non-stick face 81A of the flap adhesive cover 81 face the first flap adhesives 76 and the second flap adhesives 77 in a stretched state so that it will be able to releasably adhere to the first flap adhesive 76 and the second flap adhesives 77. When the flap fasteners 76 and 77 comprise adhesive fasteners, the non-stick face 81A can be provided by attaching a separate release paper or element to the flap adhesive cover 81 which is treated with a non-stick material, or by treating all or a portion of the flap adhesive cover 81 with a non-stick coating, such as by silicone coating a portion of the flap adhesive cover 81. Alternatively, if the flap fasteners 76 and 77 comprise mechanical fasteners, such as VELCRO fasteners, the non-stick face may be provided by a non-woven material capable of releasably engaging the mechanical fastening material. The opposing side 81B face away from the first flap adhesives 76 and the second flap adhesives 77. The opposing side 81B of the flap adhesive cover 81 need not have, and preferably does not have, a release coating thereon.

The flap adhesive cover 81, as shown in FIGS. 1, 2, 6 and 7, is joined to the main wrapper sheet 80 in a folded state. The flap adhesive cover 81 is folded about the transverse fold axis F3 so that the first portion 84 overlays the second portion 85. Alternatively, the flap adhesive cover 81 may be folded about the transverse fold axis F1. In such a case, the fold transverse axis F3 may coincide with the fold axis F1. In the folded state, the opposing side 81B faces inside and the non-stick face 81A faces outside. As shown in FIG. 6, this opposing side 81B at the first end portion 81C is joined to the second end portion 80B of the main wrapper sheet 80 by applying adhesive layer 83. In a preferred embodiment, when the flap adhesive cover 81 is folded, the first end portion 81C of the first portion 84 extends outwardly beyond the second end portion 81D of the second portion 85 and the end edge 28 of the main body portion 22 in the second region 41. In addition, the second end portion 80B of the main wrapper sheet 80 extends outwardly beyond the second end portion 81D of the second portion 85 and the end edge 28 of the main body portion 22 in the second region 41.

The flap adhesive cover 81 can be of any suitable size and shape, though the figures depict a flap adhesive cover 81 which is only of sufficient width and length to cover and protect the first flap adhesives 76 and the second flap adhesives 77.

Figure 8:
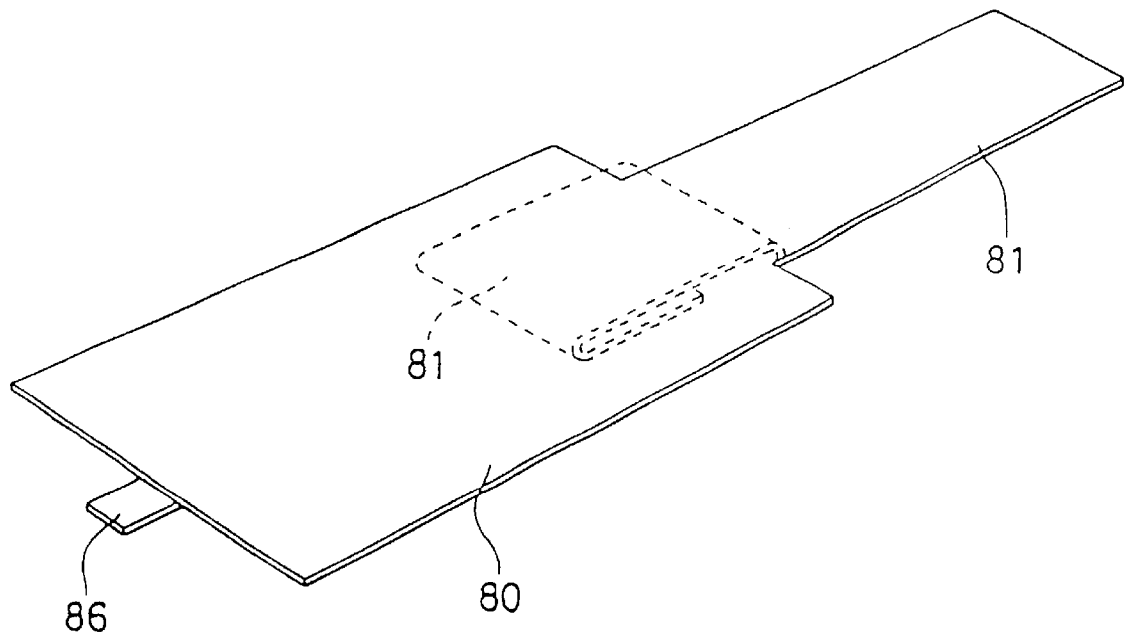
FIG. 8 is a perspective view of an alternative embodiment of the wrapper of the present invention.

FIG. 8 shows a variation of the flap adhesive cover 81 shown in the preceding drawing figures. In the embodiment shown in FIG. 8, instead of being a separate component of the main wrapper sheet 80, the flap adhesive cover 81 is an integral portion of the main wrapper sheet 80.

The wrapper 78 preferably also comprises an optional package fastener 86 for retaining the package formed by folding the wrapper and sanitary napkin in its folded configuration. The package fastener 86 is preferably both releasably attachable to the package and resealable. The package fastener 86 may be comprised of any releasably attachable and resealable fastener known in the art, such as spots or patches of adhesive, tapes, and mechanical fasteners. A tape tab with a pressure sensitive adhesive located thereon has been found to work well. The package fastener 86 can be disposed at any suitable location on the wrapper 78. In the embodiment shown in FIGS. 1 and 2, the package fastener 86 is preferably positioned at opposing first end portion 80A of the main wrapper sheet 80.

Figure 5:
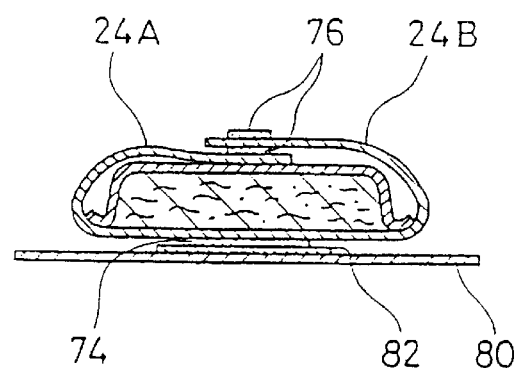
FIG. 5 is a cross-sectional view of an alternate embodiment of the flaps of the sanitary napkin in an alternative topsheet protecting position.

For the initial packaging of the sanitary napkin 20 in the wrapper 78, the garment-facing side 20B of the main body portion 22 is placed on top of the main wrapper sheet 80. The sanitary napkin 20 is positioned so that the central pad fastener 74 lies over the release paper or release coating 82 on the main wrapper sheet 80. The first flaps 24 and the second flaps 25 are then preferably folded over the topsheet 38 so that the first flaps 24 and the second flaps 25 are in the configuration shown in FIGS. 2 and 3. Folding the flaps 24 and 25 in the configuration shown in FIGS. 2 and 3 exposes the patches of adhesive 76 and 77 disposed on the garment-facing side of flaps 24 and 25 and causes the flaps 24 and 25 to cover at least a portion of the topsheet 38. Folding the flaps 24 and 25 over the topsheet 38 can, thus, be considered to provide a degree of protection to prevent the topsheet 38 from becoming soiled prior to use. In alternative embodiments, where one or both of the first flaps 24 has a greater span (that is, its dimension measured in the transverse direction), the first flaps 24 can be folded over the topsheet 38 so that one of the first flaps 24 at least partially overlays the other flap 24 as shown in FIG. 5. The first flap 24B overlays, attaches to, and protects the flap attachment means 76 of the first flap 24A. The flap adhesive cover 84 will then overlay, attach to and protect the flap fastener 76 of the first flap 24B. The second flaps 25 may have the same structure as the first flaps 24 that have a greater span.

After folding the flaps 24 and 25 over the topsheet 38, the sanitary napkin 20 and main wrapper sheet 80 will then preferably be folded into three regions that are defined by the fold axes F1 and F2 shown in FIG. 2. The fold axes F1 and F2 will divide both the sanitary napkin 20 and the main wrapper sheet 80 into three regions comprising the first region 39, the second region 41 and the third region 43. As shown in FIG. 2, the central region (the first region) 39 lies between preferred fold axes F1 and F2. The second and third regions 41 and 43 lie longitudinally outboard of the fold axes F1 and F2. As described above, the main body portion 22 is also separated at the fold axes F1 and F2 into three sections comprising the first section 36, the second section 34, and the third section 32. Each section 36, 34 and 32 generally extends in each region 39, 41 and 43 respectively.

Figure 9:
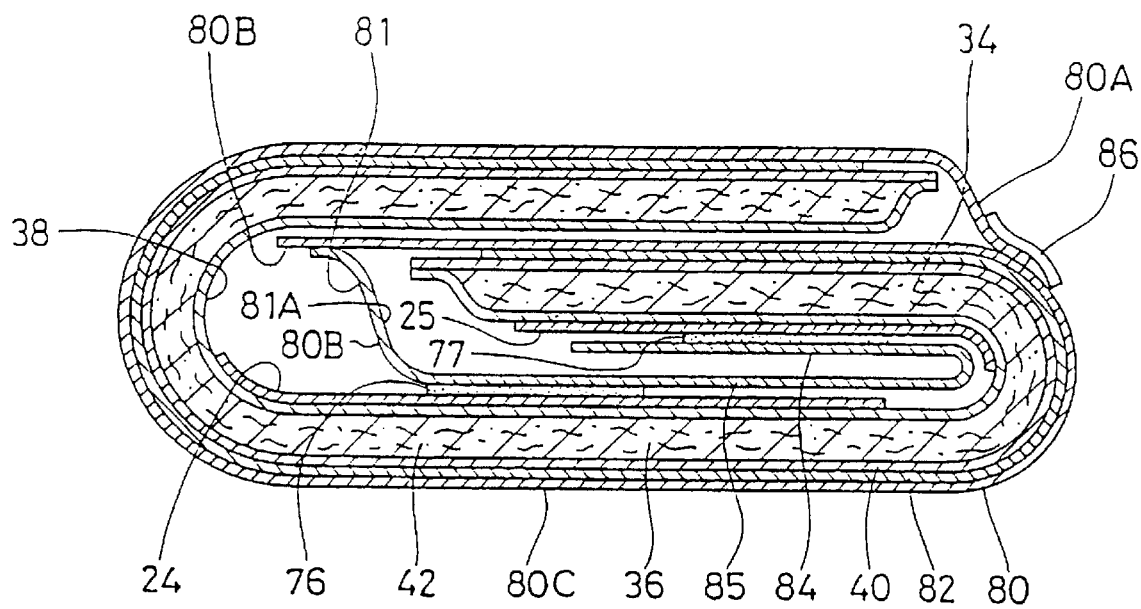
FIG. 9 is a cross-sectional view (taken along the longitudinal centerline) of one preferred wrapper of the present invention with a sanitary napkin therein in a folded configuration

FIG. 9 depicts the package for the sanitary napkin formed by folding the wrapper 78 and sanitary napkin 20 in one preferred configuration for shipment, sale, and convenient carrying by the wearer. When the second flaps 25 are folded over the topsheet 38 as stated hereinabove, the non-stick face 81A of the second portion 85 of the flap adhesive cover 81 is placed over the second flap fasteners 77 and is releasably attached to each adhesive patch 77 as shown in FIG. 2. In addition, the flap adhesive cover 81 provides a connection between each flap 25 that spans the flaps 25, thereby keeping the second flaps 25 in the desired position until the flap adhesive cover 81 is removed. As shown in FIG. 9, the second region 41 (i.e., the second end portion 80B of the main wrapper 80, along with the second section 34 of the main body portion 22, the second flaps 25, the second flap adhesives 77 and the folded flap adhesive cover 81) is folded about the fold axis F1 onto the first region 39 (i.e., the central portion 80C of the main wrapper 80, the first section 36 of the main body portion 22, the first flaps 24 and the first flap adhesives 76). When the sanitary napkin 20 and wrapper 78 are folded in this manner, the non-stick face 81A of the first portion 84 of the flap adhesive cover 81 is placed over the first flap fasteners 76 and is releasably attached to each adhesive patch 76. In addition, the flap adhesive cover 81 provides a connection between each flap 24 that spans the flaps 24, thereby keeping the first flaps 24 in the desired position until the flap adhesive cover 81 is removed. The third region 43 (i.e., the first end portion 80A of the main wrapper 80, along with the third section 32 of the main body portion 22) is then folded about the fold axis F2 onto the second region 41 which is already folded onto the first region 39. By pressing the tape tab 86 onto the exterior of wrapper 78 in the position depicted in FIG. 9, the sanitary napkin 20, its flaps 24 and 25 and wrapper 78 remain in the configuration shown.

Figure 10:
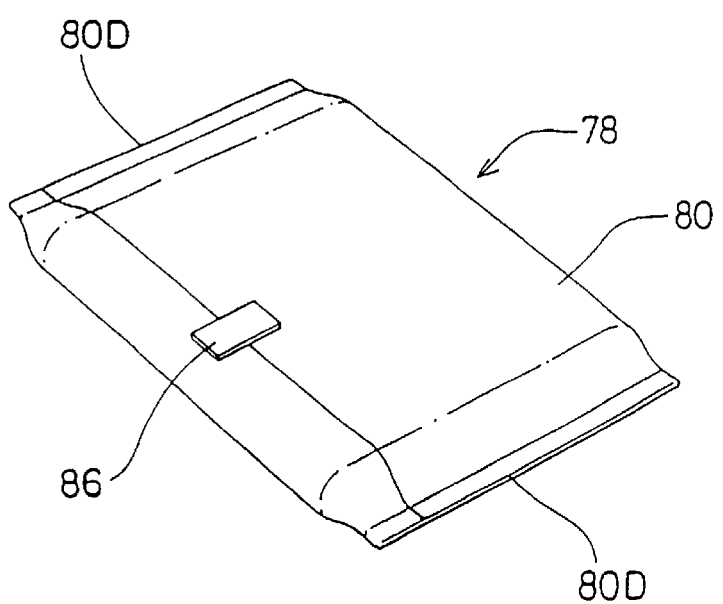
FIG. 10 is a perspective view of one preferred individually packaged absorbent article of the present invention.

Preferably, to complete the individual packaging of the sanitary napkin 20 in the wrapper 78 of the present invention, each longitudinal side edge 80D of the main wrapper sheet 80 is then frangibly sealed after the sanitary napkin 20 and the wrapper 78 are in the folded configuration shown in FIG. 9. The frangible sealing of the side edges 80D of the main wrapper sheet 80 can be accomplished by any suitable sealing technique. By way of example only, the longitudinal side edges 80D may be heat sealed, glued, or ultrasonically bonded as shown in FIG. 10. The entire sanitary napkin 20 is thereby protected until the wrapper 78 is opened. Suitable methods for frangibly sealing the longitudinal side edges are described in U.S. Pat. No. 4,556,146 issued to Swanson.

The various embodiments of the wrapper 78 described herein can be made in any suitable manner. The flap adhesive cover 81 may be made of the same material as the main wrapper sheet or any adhesive cover material known in the art. The flap adhesive cover 81, if separate elements, can be joined to the main wrapper sheet 80 at any time during the manufacture of the individually packaged sanitary napkin 20 of the present invention. Preferably, for ease of manufacture, the flap adhesive cover 81 will be joined to the main wrapper sheet 80 after the sanitary napkin 20 is already placed on the main wrapper sheet 80. This will eliminate the need to temporarily remove the flap adhesive cover 81 from the main wrapper sheet 80 to allow the sanitary napkin 20 to be placed on the main wrapper sheet 80. The release paper or release coating 82 on the main wrapper sheet 80, the non-stick surface 81A on the flap adhesive cover 81 is preferably applied before the flap adhesive cover 81 is joined to the main wrapper sheet 80.

Figure 11:
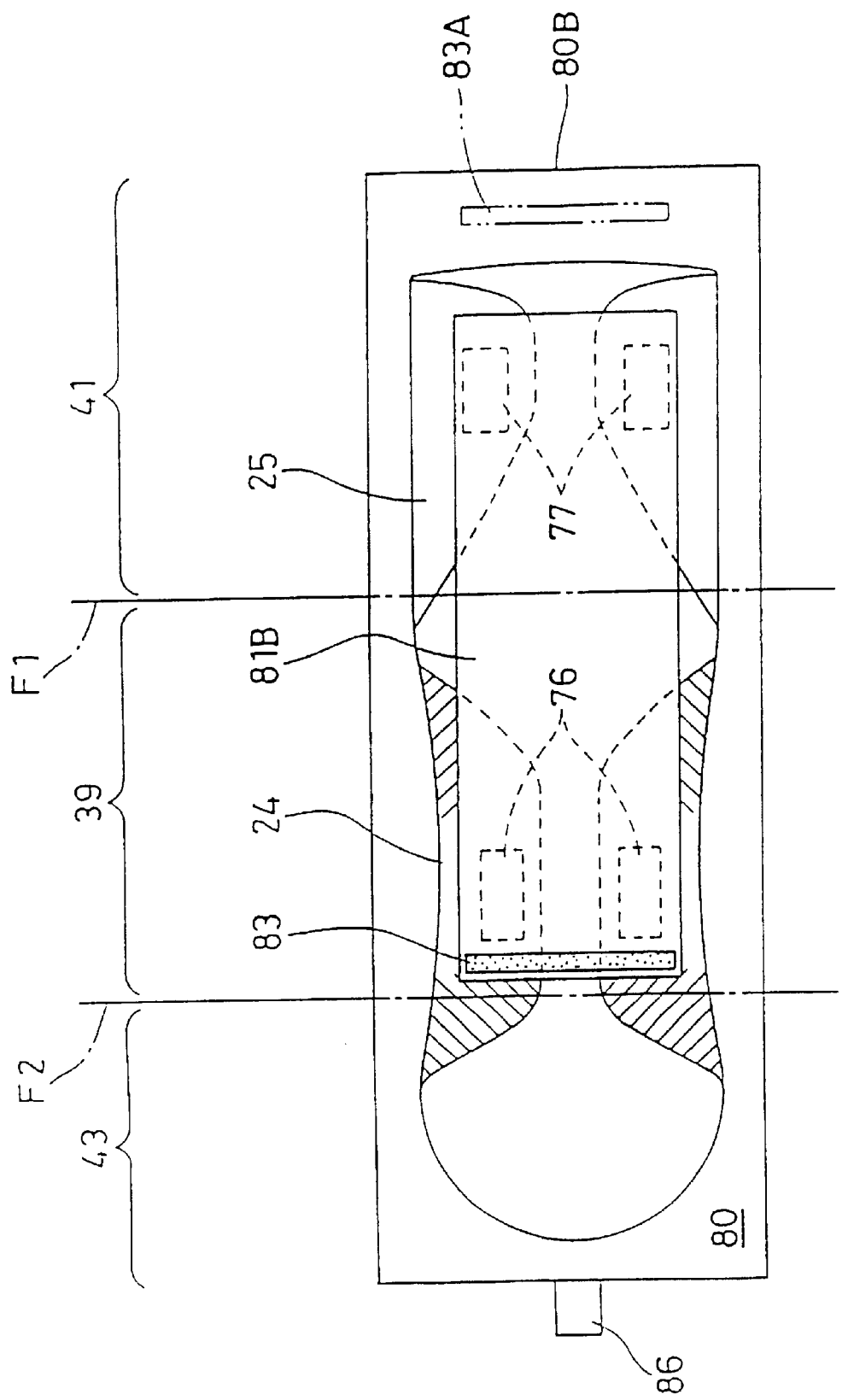
FIG. 11 is a top plan view of an alternative embodiment wrapper of the present invention with a sanitary napkin placed thereon in substantially the same configuration as FIG. 2.

More preferably, for ease of manufacture, the flap adhesive cover 81 may be placed onto the first flaps 24 and the second flaps 25 respectively as shown in FIG. 11 before the flap adhesive cover 81 is joined to the main wrapper sheet 80. The non-stick surface 81A of the flap adhesive cover 81 covers the first flap adhesives 76 and the second flap adhesives 77. In addition, the flap adhesive cover 81 covers and protects majority of the body contacting surface 20A from contamination while manufacturing the absorbent article. The opposing sides 81 B which are not treated releasably may be provided with the adhesive layer 83 either before or after the flap adhesive cover 81 is placed onto the flaps 24 and 25. Alternatively, the adhesive layer 83 may be provided with the region 83A of the main wrapper sheet 80. Then the second region 41 is folded onto the first region 39 about the fold axis F1, and the adhesive layer 83 applied to the flap adhesive cover 81 is undetachably joined to the region 83A in the second end portion 80B of the main wrapper sheet 80. After that, the third region 43 is folded onto the second region 41 which is already folded onto the first region 39. When the individual packaged sanitary napkin 20 is opened, the flap adhesive cover 81 is removed from the first flaps 24 and 25 but it stays with the first end portion 80A of the main wrapper sheet 80.

Figure 12:
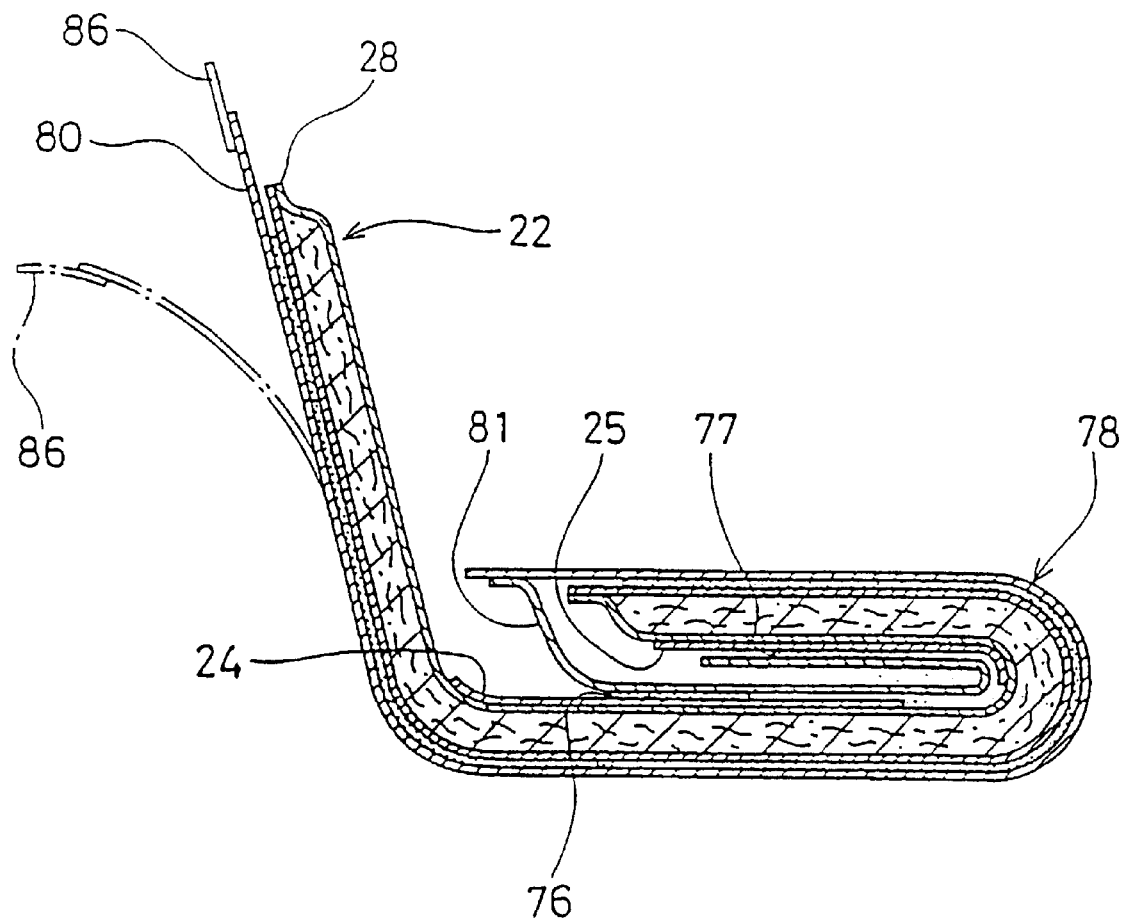
FIG. 12 is a first cross-sectional view (taken along the longitudinal centerline) of the present invention explaining an action of removing a wrapper from a sanitary napkin.
Figure 13:
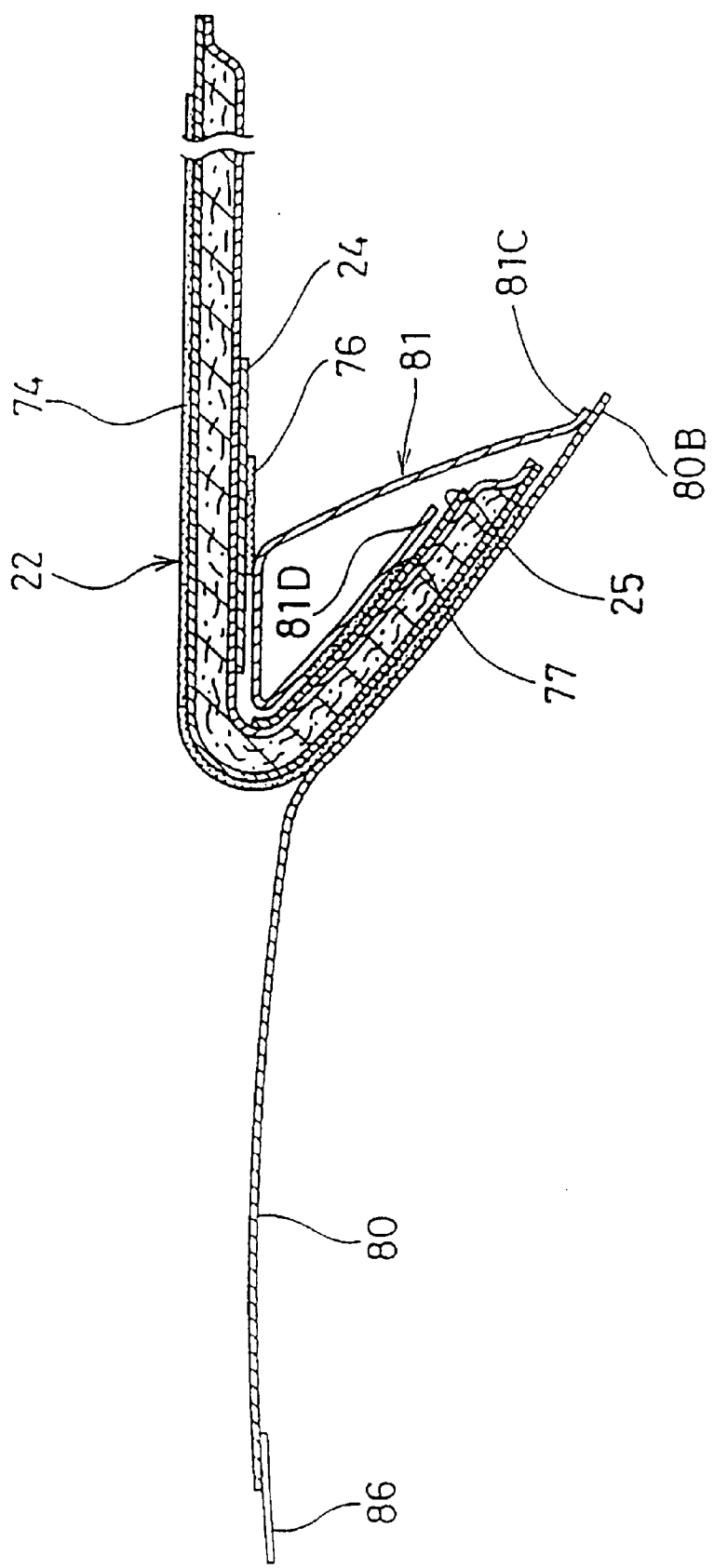
FIG. 13 is a second cross-sectional view (taken along the longitudinal centerline) of the present invention explaining an action of removing a wrapper from a sanitary napkin.
Figure 14:
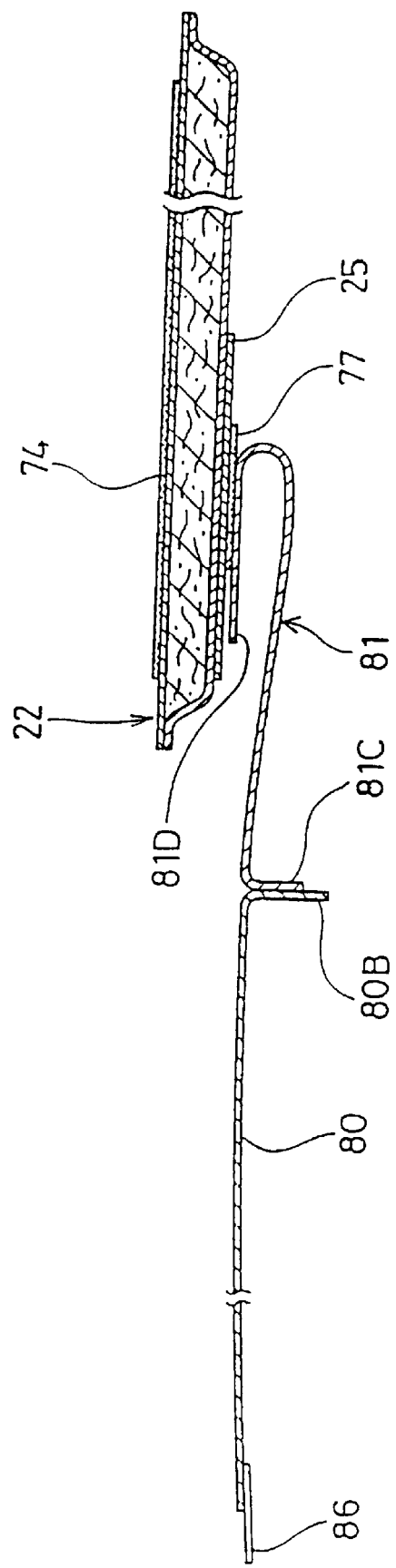
FIG. 14 is a third cross-sectional view (taken along the longitudinal centerline) of the present invention explaining an action of removing a wrapper from a sanitary napkin.

The consumer will ordinarily carry the individually packaged sanitary napkin of the present invention in the form depicted in FIGS. 9 and 10. As shown in FIG. 12, the individually packaged sanitary napkin of the present invention may be opened by peeling the tape tab 86 from the wrapper 78 and breaking the frangible seals along the longitudinal side edges 80D of the main wrapper sheet 80. This gives the consumer access to the end edge 28 of the main body portion 22 of the third region 43. The consumer may then take hold of the end edge 28 of the main body portion 22 of the third region 43 and pull the tape tab 86 from the sanitary napkin 20 as shown in FIG. 12. As the sanitary napkin 20 is separated from the wrapper 78, the central pad adhesive 74 is separated from the main wrapper sheet 80 as shown in FIG. 13. At the same time, the first flap adhesives 76 is separated from the flap adhesive cover 81. Because the first end portion 81C adjacent to the peeling starting side of the first flap adhesives 76 is joined to the second end portion 80B of the main wrapper sheet 80, it is easy and smooth to separate the first flap adhesives 76 from the flap adhesive cover 81 compared with a flap adhesive cover 81, a second end portion 81D of which is joined to the second end portion 80B of the main wrapper sheet 80 and a first end portion 81C is free. When or after the main body portion 22 separates from the main wrapper sheet 80, the second flap adhesives 77 provided on the second flaps 25 begin to separate from the flap adhesive cover 81 as shown in FIG. 14. Because the first end portion 81C adjacent to the peeling starting side of the second flap adhesives 77 is joined to the second end portion 80B of the main wrapper sheet 80, it is easy and smooth to separate the second flap adhesives 77 from the flap adhesive cover 81 compared with a flap adhesive cover 81, a second end portion 81D of which is joined to the second end portion 80B of the main wrapper sheet 80 and a first end portion 81C is free. The sanitary napkin 20 is further pulled from the wrapper 78, the sanitary napkin 20 and the wrapper 78 are separated from one another. The separation of the sanitary napkin 20 from the wrapper 78 is preferably achieved in a single motion.

Once the sanitary napkin is removed from the wrapper 78 and installed in the wearer's panties, the consumer may fold the wrapper 78, secure the wrapper 78 in its folded orientation by reattaching resealable tape tab 86 to wrapper 78. The consumer may then store the folded wrapper 78 for rewrapping and disposing of the used sanitary napkin. The wearer need not worry about collecting and disposing of loose flap adhesive release strips, that were previously required, since all release strips are attached to or integral with the wrapper 78. The present invention, therefore, provides the wearer with a clean sanitary napkin 20 which is easily installed and without extra pieces of waste which must be collected.

FIGS. 15–24 show an alternative embodiment of the present invention. The wrapper 178 shown in FIGS. 15–24 has essentially the same structure as the first embodiment above. Therefore, the portions of the alternative embodiment shown in FIGS. 15–24 which correspond to the portions of the embodiment shown in FIGS. 1–14 above are referred by the same reference numbers.

The wrapper 178 comprises the flap adhesive cover 81. The flap adhesive cover 81 covers and protects the first flap adhesives 76 and the second flap adhesives 77. The flap adhesive cover 81 comprises a single separate sheet having a first end portion 81C, a second end portion 81D and a pair of longitudinal side portions 81E. The flap adhesive cover 81 also comprises a transverse fold axis F3, a first portion 84 and a second portion 85. The first portion 84 extends from the transverse fold axis F3 toward the fold axis F2 in the first region 39 and the second portion 85 extends from the transverse fold axis F3 toward the second end portion 80B of the main wrapper 80 in the second region 41. The flap adhesive cover 81 also has two faces, one of which is a non-stick face (or releasable face) 81A, which is capable of releasable attachment with the flap fasteners, and an opposite face or side 81B.

Figure 15:
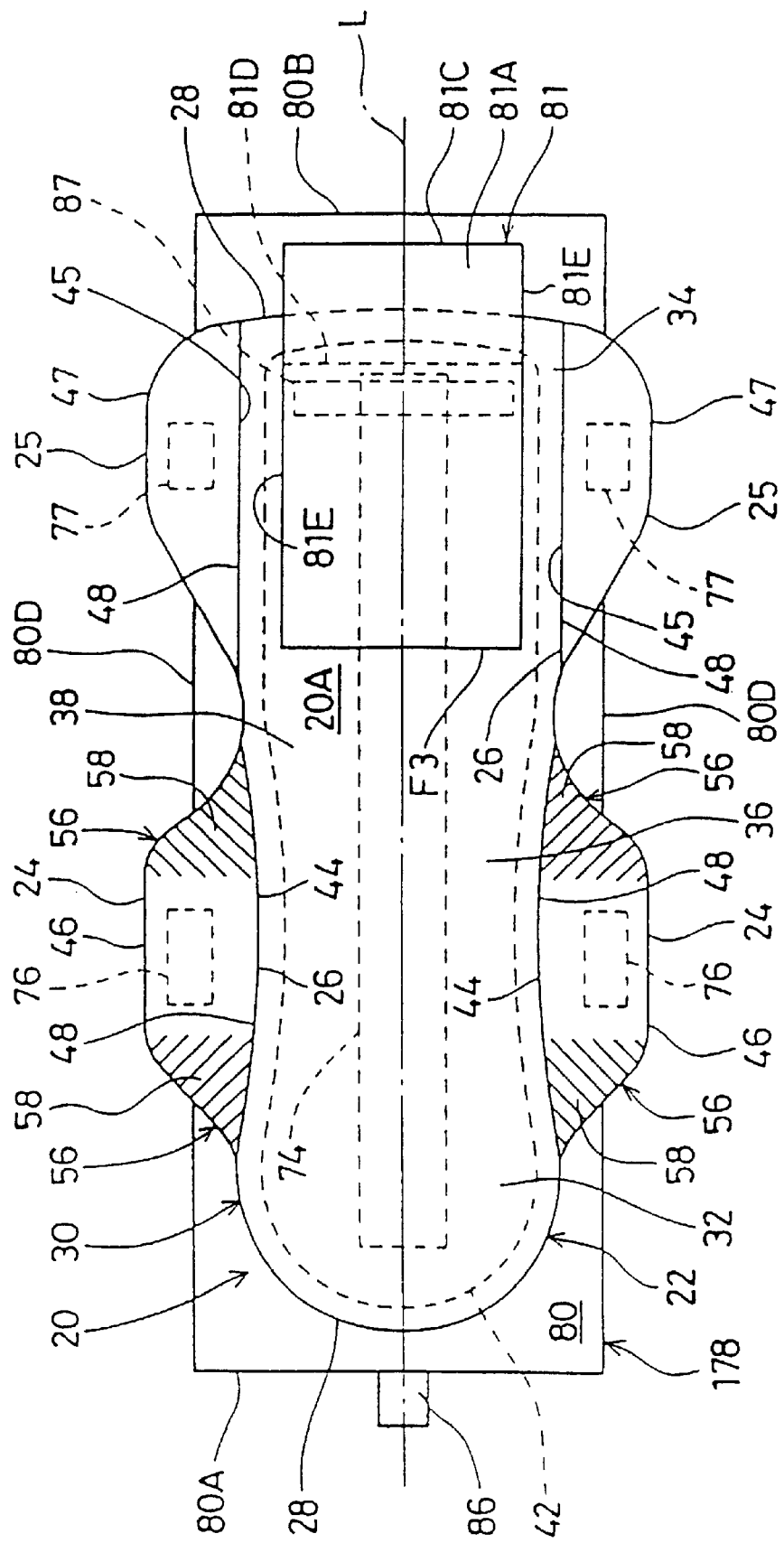
FIG. 15 is a top plan view of an alternative embodiment of the wrapper of the present invention in an opened position with a preferred sanitary napkin disposed thereon and the flaps of the sanitary napkin outstretched.
Figure 16:
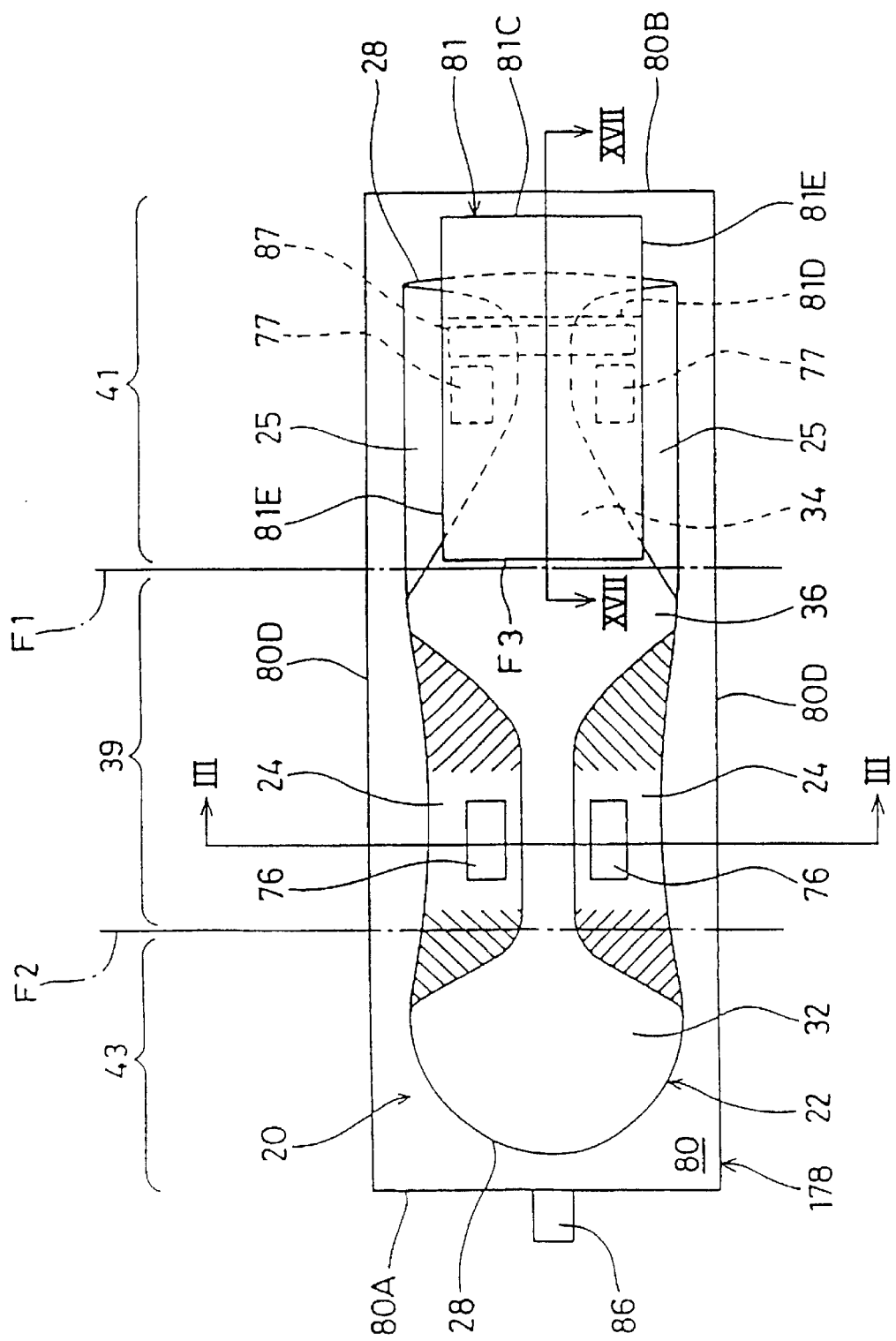
FIG. 16 is a top plan view of the wrapper of the alternative embodiment shown in FIG. 15 with the flaps of the sanitary napkin folded over the topsheet.
Figure 17:
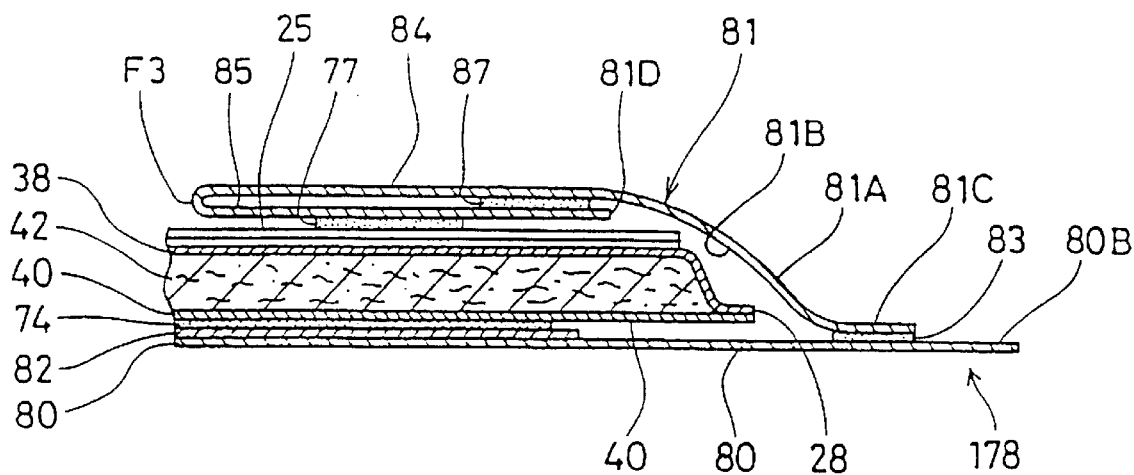
FIG. 17 is a cross-sectional view of FIG. 16 taken along the line XVII—XVII.

The flap adhesive cover 81, as shown in FIGS. 15–18 and 20, is joined to the main wrapper sheet 80 in a folded state. The flap adhesive cover 81 is folded about the transverse fold axis F3 so that the majority of the first portion 84 overlays the majority of the second portion 85 with face-to-face relation. The opposing side 81B at the first end portion 81C is joined to the second end portion 80B of the main wrapper sheet 80 by applying adhesive layer 83. In addition, the first portion 84 and the second portion 85 of the flap fastener cover 81 are joined to one another by applying adhesive layer 87 to the opposing side 81B. The adhesive layer 87 may be applied onto the opposing side 81A of either the first portion 84 or the second portion 85 and may position anywhere in the area where the first portion 84 and the second portion 85 overlap. For example, the adhesive layer 87 may position near the transverse axis F3. Preferably, the adhesive layer 87 is provided adjacent to the second end portion 81D of the second portion 85 as shown in FIGS. 15–17. In a preferred embodiment, when the flap adhesive cover 81 is folded, the first end portion 81C of the first portion 84 extends outwardly beyond the second end portion 81D of the second portion 85 and the end edge 28 of the main body portion 22 in the second region 41. Further, the second end portion 80B of the main wrapper sheet 80 extends outwardly beyond the second end portion 81D of the second portion 85 and the end edge 28 of the main body portion 22 in the second region 41.

Figure 18:
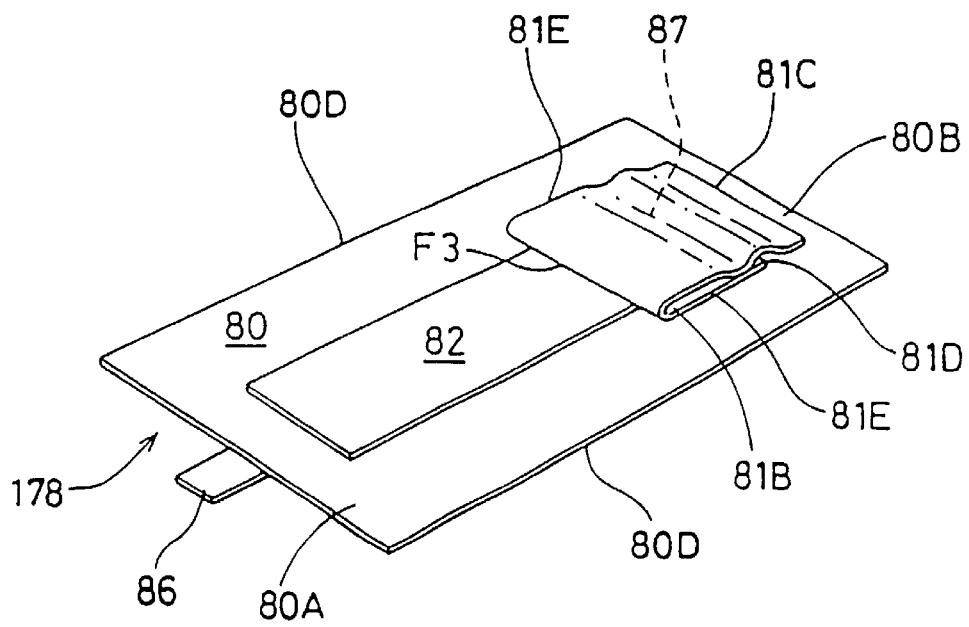
FIG. 18 is a perspective view of one preferred wrapper of the alternative embodiment shown in FIG. 15.
Figure 19:
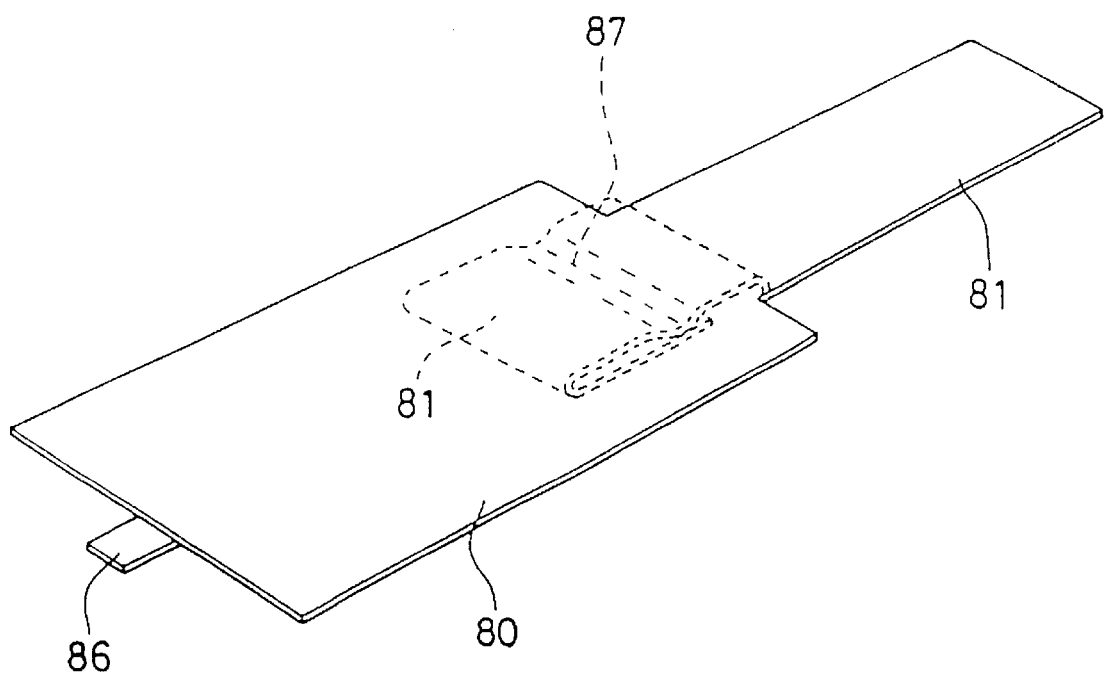
FIG. 19 is a perspective view of an alternative embodiment of the wrapper shown in FIG. 18.

FIG. 19 shows a variation of the flap adhesive cover 81 shown in FIG. 18. In the embodiment shown in FIG. 19, instead of being a separate component of the main wrapper sheet 80, the flap adhesive cover 81 is an integral portion of the main wrapper sheet 80. In this embodiment, the adhesive layer 87 is also applied to join the first portion 84 and the second portion 85.

Figure 20:
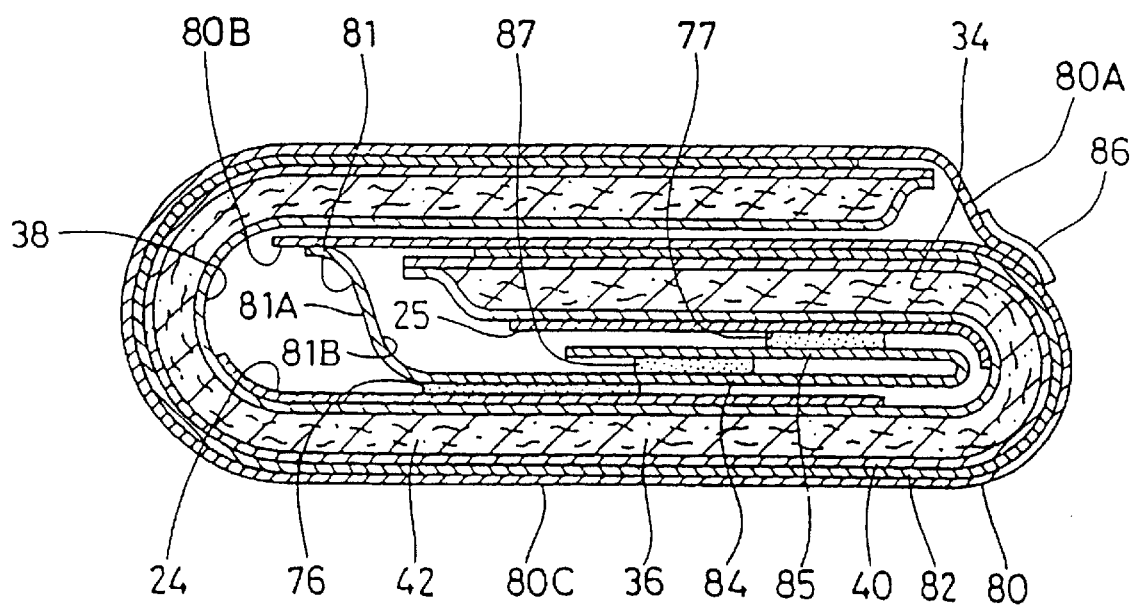
FIG. 20 is a cross-sectional view (taken along the longitudinal centerline) of one preferred wrapper of the alternative embodiment shown in FIG. 15 with a sanitary napkin therein in a folded configuration.

FIG. 20 shows the package for the sanitary napkin formed by folding the wrapper 178 and the sanitary napkin 120 in one preferred embodiment for shipment, sale and convenient carrying by the wearer, which is essentially the same as the configuration shown in FIG. 9. In the embodiment shown in FIG. 20, the adhesive layer 87 is applied to join the first portion 84 and the second portion 85.

Figure 21:
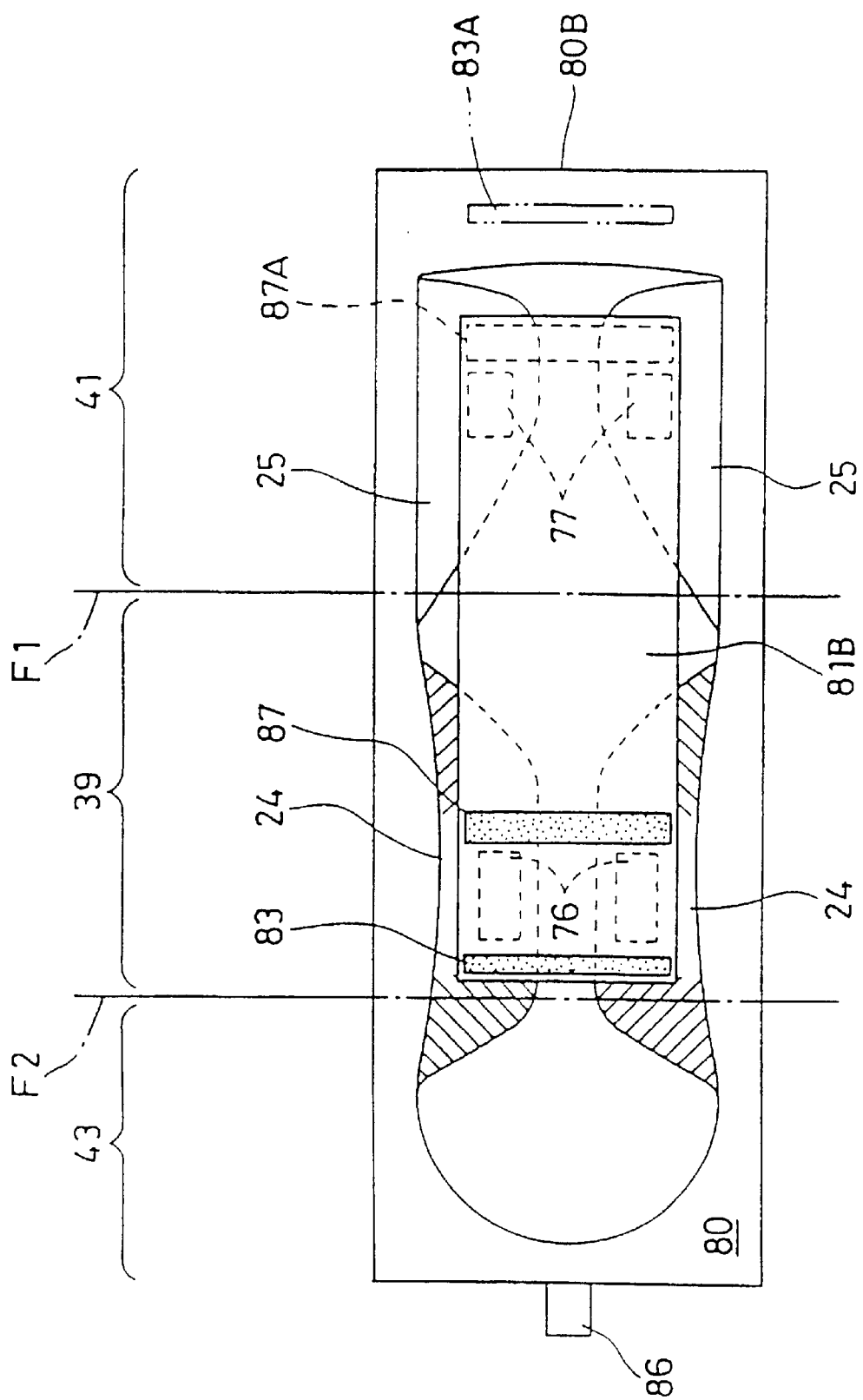
FIG. 21 is a top plan view of an alternative embodiment wrapper with a sanitary napkin placed thereon in substantially the same configuration as FIG. 16.

For ease of manufacture, the flap adhesive cover 81 may be placed onto the first flaps 24 and the second flaps 25 respectively as shown in FIG. 21 before the flap adhesive cover 81 is joined to the main wrapper sheet 80. The flap adhesive cover 81 covers and protects majority of the body contacting surface 20A from contamination while manufacturing the absorbent article. The opposing sides 81B which are not treated releasably may be provided with the adhesive layers 83 and 87 either before or after the flap adhesive cover 81 is, placed onto the flaps 24 and 25. Alternatively, the adhesive layers 83 and 87 may be provided with the regions 83A and 87A of the main wrapper sheet 80. Then the second region 41 is folded onto the first region 39 about the fold axis F1, and the adhesive layer 83 applied to the flap adhesive cover 81 is undetachably joined to the region 83A in the second end portion 80B of the main wrapper sheet 80, and the adhesive layer 87 applied to one of the first portion 84 and the second portion 85 is undetachably joined to the other portion. After that, the third region 43 is folded onto the second region 41 which is already folded onto the first region 39.

Figure 22:
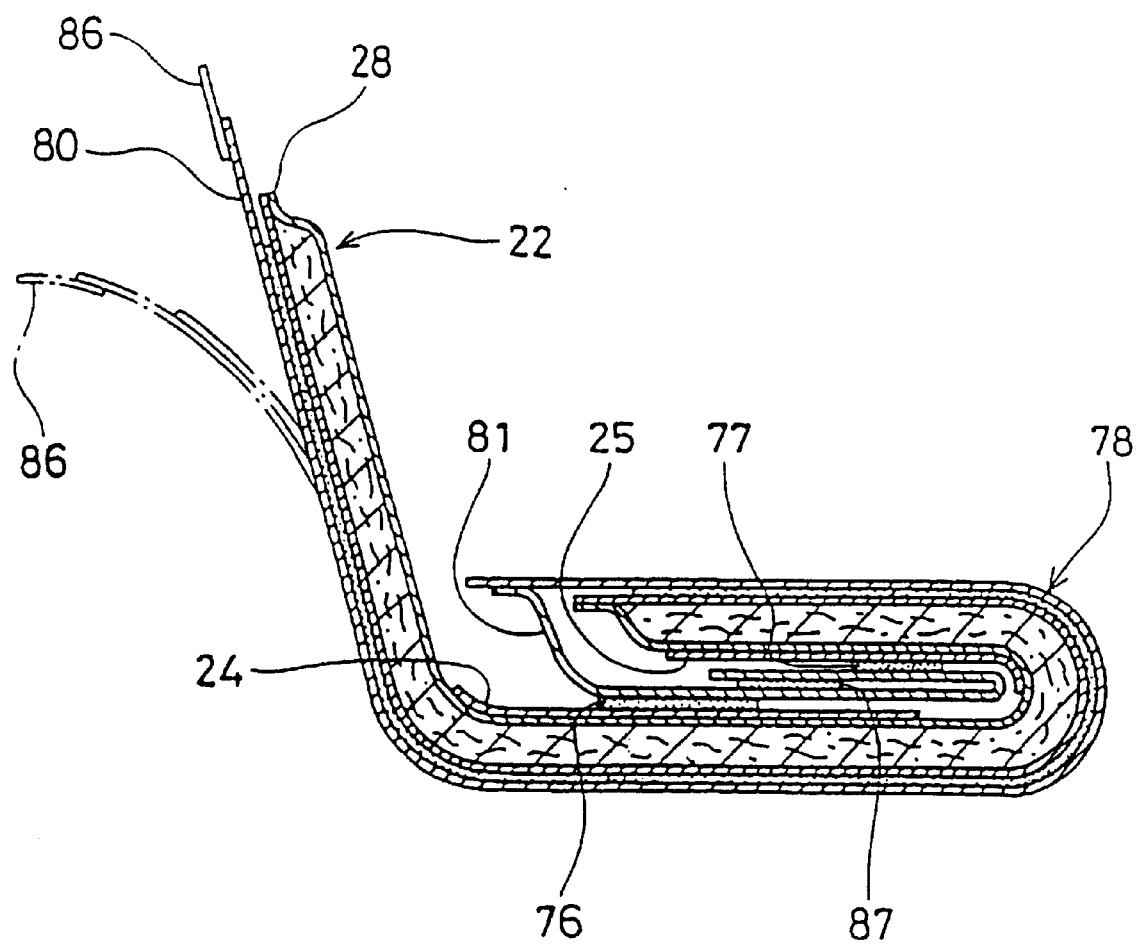
FIG. 22 is a first cross-sectional view (taken along the longitudinal centerline) of the alternative embodiment explaining an action of removing a wrapper from a sanitary napkin.
Figure 23:
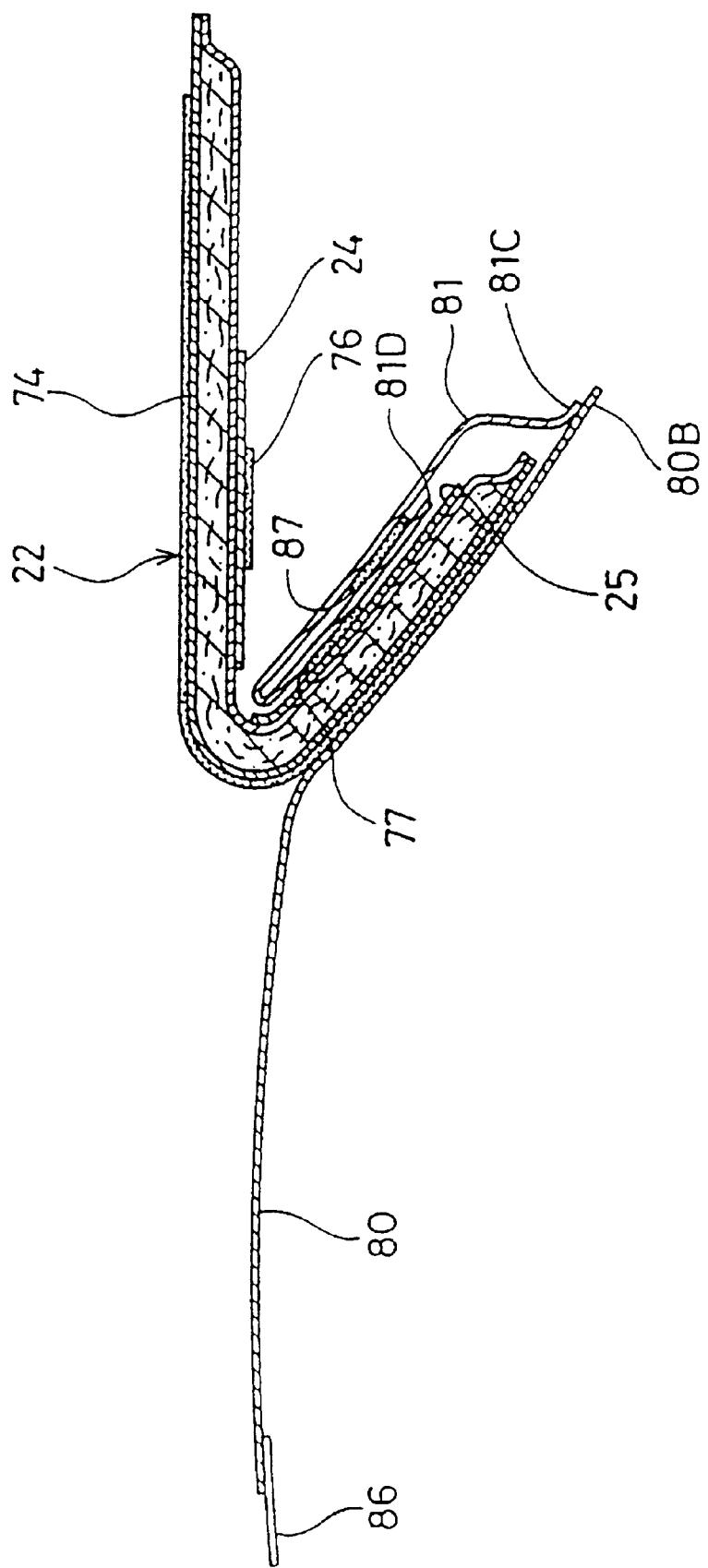
FIG. 23 is a second cross-sectional view (taken along the longitudinal centerline) of the alternative embodiment explaining an action of removing a wrapper from a sanitary napkin.
Figure 24:
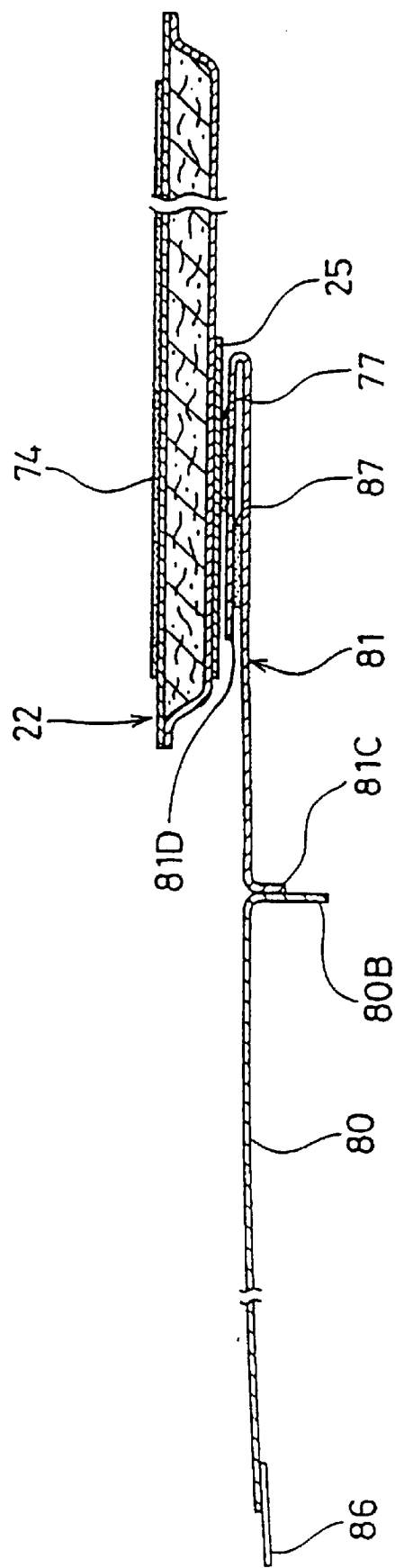
FIG. 24 is a third cross-sectional view (taken along the longitudinal centerline) of the alternative embodiment explaining an action of removing a wrapper from a sanitary napkin.

As shown in FIG. 22, the individually packaged sanitary napkin of the present invention may be opened by peeling the tape tab 86 from the wrapper 178. The consumer may then take hold of the end edge 28 of the main body portion 22 of the third region 43 and pull the tape tab 86 from the sanitary napkin 20 as shown in FIG. 22. As the sanitary napkin 20 is separated from the wrapper 178, the central pad adhesive 74 is separated from the main wrapper sheet 80. As further separated, the first flap adhesives 76 is separated from the flap adhesive cover 81 as shown in FIG. 23. After that, the second flap adhesives 77 provided on the second flaps 25 begin to separate from the flap adhesive cover 81 as shown in FIG. 24. The sanitary napkin 20 is further pulled from the wrapper 178, the sanitary napkin 20 and the wrapper 178 are separated from one another. The separation of the sanitary napkin 20 from the wrapper 178 is preferably achieved in a single motion. Because the first portion 84 and the second portion 85 are joined to one another by the adhesive layer 87 in the folded state, this minimizes the operation length to separate the flap adhesive cover 81 from the first flap adhesive 76 and the second flap adhesives 77.

Figure 25:
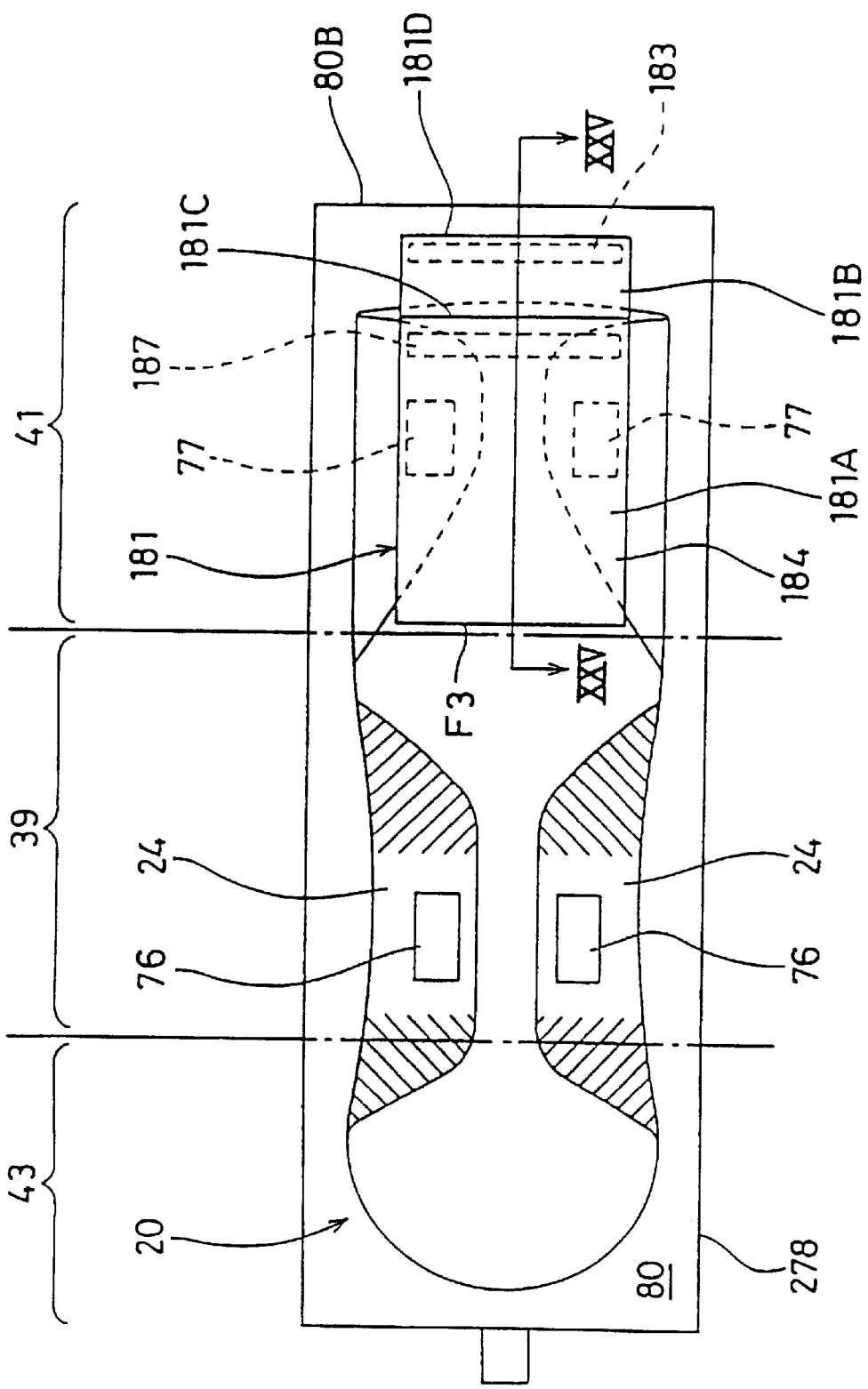
FIG. 25 is a top plan view of an alternative embodiment of the present invention with the flaps of the sanitary napkin folded over the topsheet.
Figure 26:
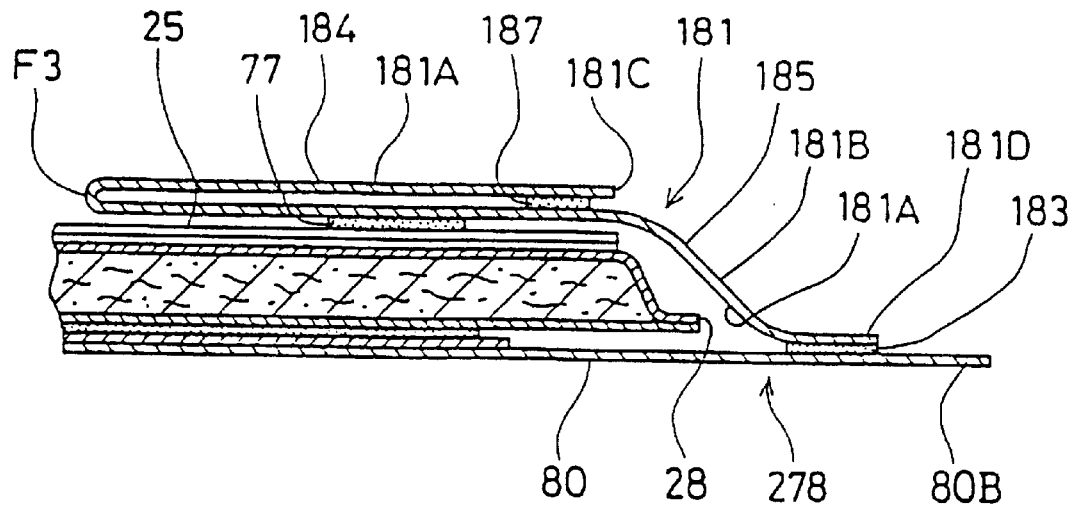
FIG. 26 is a cross-sectional view of FIG. 25 taken along the line XXV—XXV.
Figure 27:
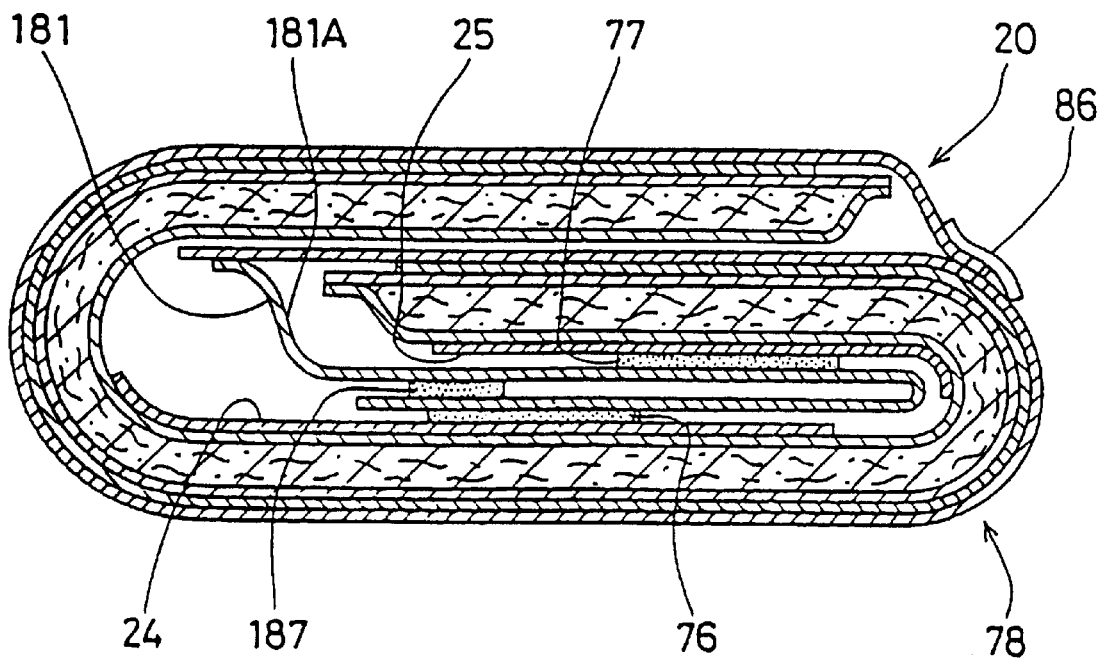
FIG. 27 is a cross-sectional view (taken along the longitudinal centerline) of the alternative embodiment shown in FIG. 25 with a sanitary napkin therein in a folded configuration.

FIGS. 25–27 shows an alternative embodiment wrapper 278 of the present invention. In this embodiment, the flap adhesive cover 181 also may extend from the second end portion 80B of the main wrapper sheet 80 and extend in the second region 41 in a folded state. The flap adhesive cover 181 has two faces comprising a top face 181A and an opposite face or side 181B. Only a part of the top face 181A may be a non-stick area (or releasable face) which is capable of releasable attachment with the flap fasteners. Preferably, the non-stick area of the top face 181A of the flap adhesive cover 181 faces the first flap adhesives 76 and the second flap adhesives 77 so that it will be able to releasably adhere to the first flap adhesive 76 and the second flap adhesives 77. Preferably, an area of the top face 181A where the adhesive layer 183 is applied is not releasably treated.

The flap adhesive cover 181 is joined to the main wrapper sheet 80 in a folded state. As shown in FIG. 25–27, the flap adhesive cover 181 may be joined to the second end portion 80B of the main wrapper sheet 80 at the second end portion 181D of the second portion by applying adhesive layer 183 onto the non-releasably treated area of the top face 181A. The adhesive layer 187 to join the first portion 184 and the second portion 185 of the flap fastener cover 81 with face-to-face relation may be applied onto the opposing face 181B of either the first portion 184 or the second portion 185. The adhesive layer 187 may be provided adjacent to the first end portion 181C, preferably adjacent to the second end portion 181D of the second portion 185. In a preferred embodiment, when the flap adhesive cover 181 is folded, the second end portion 80B of the main wrapper sheet 80 may extend beyond the end edge 28 of the main body portion 22 in the second region 41.

FIG. 27 depicts the package for the sanitary napkin formed by folding the wrapper 278 and sanitary napkin 20 in one preferred configuration for shipment, sale, and convenient carrying by the wearer. When the second flaps 25 are folded over the topsheet 38 as stated hereinabove, the non-stick area of the top face 181A of the flap adhesive cover 181 is placed over the second flap fasteners 77. As shown in FIG. 27, the second region 41 is folded about the fold axis F1 onto the first region 39. When the sanitary napkin 20 and wrapper 278 are folded in this manner, the non-stick area of the top face 181A of the flap adhesive cover 181 is placed over the first flap fasteners 76. The third region 43 is then folded about the fold axis F2 onto the second region 41 which is already folded onto the first region 39. The tape tab 86 may be provided. The embodiment shown in FIGS. 25–27 minimizes the operation length to separate the flap adhesive cover 181 from the flap adhesives 76 and 77. In this embodiment, the separation of the sanitary napkin 20 from the wrapper 278 is preferably achieved in a single motion.

The disclosures of all patents, patent applications (and any patents which issue thereon, as well as any corresponding published foreign patent application), and publications mentioned throughout this description are hereby incorporated by reference herein. It is expressly not admitted, however, that any of the documents incorporated by reference herein teach or disclose the present invention.

It is to be recognized that the foregoing detailed description of the preferred embodiment of the present invention is given merely by way of illustration, and that numerous modifications and variations may become apparent to those skilled in the art without departing from the spirit and scope of the invention. Therefore, the scope of the present invention is to be determined by reference to the appended claims.

What is claimed is:

1. An individually packaged absorbent article comprising:
(a) an absorbent article extending in a longitudinal direction and comprising a main body portion having a pair of longitudinal side edges, a pair of end edges, a garment surface, and a body surface, wherein the garment surface of the main body portion may be placed in a wearer's undergarment, and the absorbent article comprises a pair of first flaps joined to the main body portion and extending laterally outward beyond the longitudinal side edges of the main body portion and a pair of second flaps joined to the main body portion apart from the first flaps in the longitudinal direction and extending laterally outward beyond the longitudinal side edges of the main body portion, wherein the garment surface of each of the first and second flaps comprises a first flap fastener and a second flap fastener respectively, and the first and second flaps are folded over the body surface of the main body portion to expose the flap fasteners;
(b) a wrapper for the absorbent article, the wrapper comprising a main wrapper sheet and a flap fastener cover, wherein
(c) the main wrapper sheet comprises a pair of longitudinal side portions, a pair of end portions, an inner surface facing the main body portion and an outer surface, the main wrapper sheet is positioned adjacent to the garment surface of the main body portion, the main wrapper sheet and the main body portion of the absorbent article comprise two transverse axes and three regions divided by the two axes, wherein the three regions comprise a first region into which a majority of the first flaps extends, a second region into which a majority of the second flaps extends and a third region, and the two transverse axes comprise the first axis extending laterally between the first region and the second region and the second axis extending laterally between the first region and the third region,
(d) the flap fastener cover comprises a pair of longitudinal side portions, a pair of end portions, a releasable surface facing the flap fasteners of the first and second flaps, an opposing surface, a first portion, and a second portion, wherein a majority of the first portion extends in the first region and a majority of the second portion extends in the second region when the absorbent article is folded at the transverse axes, and the flap fastener cover is releasably affixed to the flap fasteners of the first and second flaps,
(e) the end portion of the first portion of the flap fastener cover is joined to the end portion of the main wrapper sheet of the second region.

2. The absorbent article of claim 1 wherein the flap fastener cover comprises a single separate element joined to the main wrapper sheet.

3. The absorbent article of claim 1 wherein the main wrapper sheet and the main body portion of the absorbent article are folded as a unit about the first axis so that the second region superposes the first region, and the flap fastener cover is interposed between the first region and the second region.

4. The absorbent article of claim 3 wherein the flap fastener cover further comprises a transverse axis dividing the flap fastener cover into the first portion and the second portion, wherein the flap fastener cover is folded about the transverse axis, the first portion of the flap fastener cover extends from the transverse axis towards the second axis, the second portion of the flap fastener cover extends from the transverse axis towards the end port ion of the main wrapper sheet of the second region, wherein the end portion of the first portion of the flap fastener cover extends beyond the end portion of the second portion of the flap fastener cover.

5. The absorbent article of claim 4 wherein the end portion of the main wrapper sheet of the second region extends beyond the end portion of the second portion of the flap fastener cover.

6. The absorbent article of claim 5 wherein the end portion of the first portion of the flap fastener cover extends beyond the end edge of the main body portion of the second region.

7. The absorbent article of claim 6 wherein the longitudinal side portions of the main wrapper sheet extend beyond the longitudinal side edges of the main body portion of the absorbent article, the end portion of the main wrapper sheet of the second region extends beyond the end edge of the main body portion of the second region.

8. The absorbent article of claim 4 wherein the opposing surface of the end portion of the flap fastener cover is joined to the inner surface of the end portion of the main wrapper sheet.

9. The absorbent article of claim 3 wherein the third region is folded onto the second region about the second axis so that the main body portion of the third region faces the outer surface of the main wrapper sheet of the second region.

10. The absorbent article of claim 1 wherein the main wrapper sheet and the flap fastener cover can be removed from both the main body portion of the absorbent article and the flaps in a single motion.

11. An individually packaged absorbent article comprising:

(a) an absorbent article extending in a longitudinal direction and comprising a main body portion having a pair of longitudinal side edges, a pair of end edges, a garment surface, and a body surface, wherein the garment surface of the main body portion may be placed in a wearer's undergarment, and the absorbent article comprises a pair of first flaps joined to the main body portion and extending laterally outward beyond the longitudinal side edges of the main body portion and a pair of second flaps joined to the main body portion apart from the first flaps in the longitudinal direction and extending laterally outward beyond the longitudinal side edges of the main body portion, wherein the garment surface of each of the first and second flaps comprises a first flap fastener and a second flap fastener respectively, and the first and second flaps are folded over the body surface of the main body portion to expose the flap fasteners;

(b) a wrapper for the absorbent article, the wrapper comprising a main wrapper sheet and a flap fastener cover, wherein (c) the main wrapper sheet comprises a pair of longitudinal side portions, a pair of end portions, an inner surface facing the main body portion and an outer surface, the main wrapper sheet is positioned adjacent to the garment surface of the main body portion, the main wrapper sheet and the main body portion of the absorbent article comprise two transverse axes and three regions divided by the two axes, wherein the three regions comprise a first region into which a majority of the first flaps extends, a second region into which a majority of the second flaps extends and a third region, and the two transverse axes comprise the first axis extending laterally between the first region and the second region and the second axis extending laterally between the first region and the third region, (d) the flap fastener cover comprises a pair of longitudinal side portions, a pair of end portions, a top surface facing the flap fasteners of the first and second flaps, an opposing surface, a first portion, and a second portion, wherein a majority of the first portion extends in the first region and a majority of the second portion extends in the second region when the absorbent article is folded at the transverse axes, and the flap fastener cover is releasably affixed to the flap fasteners of the first and second flaps, (e) the first portion and the second portion of the flap fastener cover are joined to one another so that the majority of the first portion of the flap fastener cover is disposed on the majority of the second portion of the flap fastener cover with face-to-face relation, and (f) one of the end portions of the flap fastener cover is joined to the end portion of the main wrapper sheet of the second region.

12. The absorbent article of claim 11 wherein the flap fastener cover comprises a single separate element joined to the main wrapper sheet.

13. The absorbent article of claim 11 wherein the main wrapper sheet and the main body portion of the absorbent article are folded as a unit about the first axis so that the second region superposes the first region, and the flap fastener cover is interposed between the first region and the second region.

14. The absorbent article of claim 13 wherein the flap fastener cover further comprises a transverse axis dividing the flap fastener cover into the first portion and the second portion, wherein the flap fastener cover is folded about the transverse axis, the first portion of the flap fastener cover extends from the transverse axis towards the second axis, the second portion of the flap fastener cover extends from the transverse axis towards the end portion of the main wrapper sheet of the second region, wherein the end portion of the first portion of the flap fastener cover extends beyond the end portion of the second portion of the flap fastener cover and is joined to the end portion of the main wrapper sheet of the second region.

15. The absorbent article of claim 14 wherein the longitudinal side portions of the main wrapper sheet extend beyond the longitudinal side edges of the main body portion of the absorbent article, the end portion of the main wrapper sheet of the second region extends beyond the end edge of the main body portion of the second region and the end portion of the second portion of the flap fastener cover.

16. The absorbent article of claim 15 the first portion and the second portion of the flap fastener cover are joined to one another at the point adjacent to the end portion of the second portion of the flap fastener cover.

17. The absorbent article of claim 13 wherein the flap fastener cover further comprises a transverse axis dividing the flap fastener cover into the first portion and the second portion, wherein the flap fastener cover is folded about the transverse axis, the first portion of the flap fastener cover extends from the transverse axis towards the second axis, the second portion of the flap fastener cover extends from the transverse axis towards the end portion of the main wrapper sheet of the second region, wherein the end portion of the second portion of the flap fastener cover is joined to the end portion of the main wrapper sheet of the second region.

18. The absorbent article of claim 17 wherein the longitudinal side portions of the main wrapper sheet extend beyond the longitudinal side edges of the main body portion of the absorbent article, the end portion of the main wrapper sheet of the second region extends beyond the end edge of the main body portion of the second region.

19. The absorbent article of claim 18 the first portion and the second portion of the flap fastener cover are joined to one another at the point adjacent to the end portion of the second portion of the flap fastener cover.

20. The absorbent article of claim 13 wherein the third region is folded onto the second region about the second axis so that the main body portion of the third region faces the outer surface of the main wrapper sheet of the second region.

* * * * *